(12) United States Patent
Zhang et al.

(10) Patent No.: US 12,266,426 B2
(45) Date of Patent: Apr. 1, 2025

(54) METHOD FOR ADMINISTERING A CANCER TREATMENT

(71) Applicant: ILLUMINA, INC., San Diego, CA (US)

(72) Inventors: Shile Zhang, San Diego, CA (US); Mengchi Wang, La Jolla, CA (US); Aaron Wise, San Diego, CA (US); Han Kang, San Diego, CA (US); Vitor Ferreira Onuchic, San Diego, CA (US); Kristina Kruglyak, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1127 days.

(21) Appl. No.: 16/208,149

(22) Filed: Dec. 3, 2018

(65) Prior Publication Data
US 2020/0176083 A1    Jun. 4, 2020
US 2023/0245724 A9    Aug. 3, 2023

Related U.S. Application Data

(60) Provisional application No. 62/593,802, filed on Dec. 1, 2017.

(51) Int. Cl.
| | | |
|---|---|---|
| G16B 40/20 | (2019.01) | |
| C12Q 1/6886 | (2018.01) | |
| G06F 17/15 | (2006.01) | |
| G06F 17/16 | (2006.01) | |
| G06F 17/18 | (2006.01) | |
| G16B 45/00 | (2019.01) | |
| G16B 50/20 | (2019.01) | |
| G16B 50/30 | (2019.01) | |
| G16H 50/20 | (2018.01) | |
| G16H 50/50 | (2018.01) | |

(52) U.S. Cl.
CPC ........... *G16B 40/20* (2019.02); *C12Q 1/6886* (2013.01); *G06F 17/153* (2013.01); *G06F 17/16* (2013.01); *G06F 17/18* (2013.01); *G16B 45/00* (2019.02); *G16B 50/20* (2019.02); *G16B 50/30* (2019.02); *G16H 50/20* (2018.01); *G16H 50/50* (2018.01)

(58) Field of Classification Search
None
See application file for complete search history.

(56) References Cited

U.S. PATENT DOCUMENTS

| | | |
|---|---|---|
| D506,473 S | 6/2005 | Segal et al. |
| D708,636 S | 7/2014 | Wolfe et al. |
| D736,780 S | 8/2015 | Wang |
| 9,454,286 B1 * | 9/2016 | Perttunen ............ G06F 3/0482 |
| D779,550 S | 2/2017 | Yang et al. |
| D783,673 S | 4/2017 | Xu |
| D783,674 S | 4/2017 | Yang et al. |
| D786,273 S | 6/2017 | Battin |
| D806,739 S | 1/2018 | Blackman et al. |
| D807,384 S | 1/2018 | Quattrocchi et al. |
| D835,143 S | 12/2018 | Kim et al. |
| D854,551 S | 7/2019 | Pistiner et al. |
| D863,338 S | 10/2019 | Antihi |
| D871,435 S | 12/2019 | Tseng |
| D877,747 S | 3/2020 | Belliveau |
| D877,748 S | 3/2020 | Yamazaki et al. |
| D877,749 S | 3/2020 | Yamazaki et al. |
| 10,649,611 B2 | 5/2020 | Rauschenbach et al. |
| 10,656,805 B2 | 5/2020 | Mehta et al. |
| D896,241 S | 9/2020 | Zhang et al. |
| 2015/0022674 A1 | 1/2015 | Blair et al. |
| 2017/0060520 A1 | 3/2017 | Cohen et al. |
| 2017/0283873 A1 | 10/2017 | Rico et al. |
| 2018/0224836 A1 | 8/2018 | Oka |
| 2018/0226153 A1 | 8/2018 | Rubenstein et al. |
| 2018/0238884 A1 | 8/2018 | Bass et al. |
| 2018/0242906 A1 | 8/2018 | Madabhushi et al. |

(Continued)

FOREIGN PATENT DOCUMENTS

| | | |
|---|---|---|
| JP | D1432608 S | 1/2012 |
| KR | 300903879 | 4/2017 |

(Continued)

OTHER PUBLICATIONS

Geeleher et al. (Genome Biology 2014, 15:R47, pp. 1-12) (Year: 2014).*
Jiang et al. (Genome Biology, 2016, 17:144, pp. 1-13). (Year: 2016).*
Van Allen et al. (Science. Oct. 9, 2015; 350(6257): 207-211) (Year: 2015).*
Lipson et al. (Clin Cancer Res. Nov. 15, 2011; 17(22): 6958-6962). (Year: 2011).*
Simon et al. (Journal of Statistical Planning and Inference, 2008, 138, pp. 308-320) (Year: 2008).*
PCT/US2018/063658 , "International Search Report", Mar. 18, 2019.
Barbie et al., Systematic RNA interference reveals that oncogenic KRAS-driven cancers require TBK1, HHS Public Access, May 5, 2010, pp. 108-112.

(Continued)

*Primary Examiner* — Pablo S Whaley
(74) *Attorney, Agent, or Firm* — Heslin, Rothenberg, Farley & Mesiti P.C.

(57) ABSTRACT

Provided is a computer-implemented method, including inputting to a trained machine learning classifier genomic information of a non-training subject that includes features from a tumor sample, wherein the trained machine learning classifier trained on features of tumor samples obtained from training subjects and their a responsiveness to checkpoint inhibition treatment and the machine-learning classifier is trained to predict responsiveness to the treatment, and generating a checkpoint inhibition responsiveness classification predictive of the subject's responding to the checkpoint inhibition with the trained machine-learning classifier, and reporting the checkpoint inhibition responsiveness classification using a graphical user interface. Also provided are a computer system for performing the method and a machine learning classifier trained by the method.

16 Claims, 14 Drawing Sheets

(56) References Cited

U.S. PATENT DOCUMENTS

| | | |
|---|---|---|
| 2018/0259944 A1 | 9/2018 | Oka |
| 2018/0261328 A1 | 9/2018 | Burton et al. |
| 2018/0282817 A1 | 10/2018 | You et al. |
| 2018/0291459 A1 | 10/2018 | Al-Deen Ashab et al. |
| 2018/0315507 A1 | 11/2018 | Mortazavi et al. |
| 2018/0321242 A1 | 11/2018 | Brandon et al. |
| 2020/0090087 A1 | 3/2020 | Singh |

FOREIGN PATENT DOCUMENTS

| | | | |
|---|---|---|---|
| RU | 2155373 C2 | 8/2000 | |
| RU | 2015148763 A1 | 5/2017 | |
| WO | 2015184061 A2 | 12/2015 | |
| WO | WO-2017013436 A1 * | 1/2017 | ........... C12Q 1/6886 |
| WO | 2017167942 A1 | 10/2017 | |
| WO | 2017201165 A1 | 11/2017 | |

OTHER PUBLICATIONS

Hugo et al., Genomic and Transcriptomic Features of Response to Anti-PD-1 Therapy in Metastatic Melanoma, Cell Press Article, vol. 165, Mar. 3, 2016, pp. 35-44.

Van Allen et al., Genomic correlates of response to CTLA4 blockade in metastatic melanoma, Sciencexpress Report, Sep. 10, 2015, pp. 1-30.

Charoentong et al., Pan-cancer Immunogenomic Analyses Reveal Genotype-Immunophenotype Relationships and Predictors of Response to Checkpoint Blockade, Cell Reports Resource, Jan. 3, 2017, pp. 248-262.

Finotello et al., Quantifying tumor-infiltrating immune cells from transcriptomics data, Cancer Immunology, Immunotherapy, Dec. 11, 2017, pp. 1031-1040.

Danaher et al., Gene expression markers of Tumor Infiltrating Leukocytes, Journal for Immuno Therapy of Cancer, Research Article, Feb. 21, 2017, pp. 1-15.

Rooney et al., Molecular and Genetic Properties of Tumors Associated with Local Immune Cytolytic Activity, Cell Article, Jan. 1, 2015, pp. 48-61.

Fitbark Inc., "Function related to exercise for smartphone software," website address https://itunes.apple.com/jp/app/fitbark/id937936853?mt=8; published on Feb. 26, 2016.

Carrot Rocket Ltd., "Information provision function for smartphone software," website address https://itunes.apple.com/jp/app/geozilla-zi-gongno-jian-shouri/id981856216?mt=8; published on Aug. 17, 2016.

Fabriqate Google, "Function of weather forecast for smartphone software, " website address https://play.google.com/store/apps/details?id=com.fabriqate.stateair; published on Aug. 8, 2014.

Xer.Lee. "Chart Ulkit." Dribbble, published Apr. 23, 2016 (Retrieved from the internet Jun. 15, 2020). Internet URL: <https://dribbble.com/shots/2670411-Chart-Ulkit> (Year: 2016).

Hladik, David. "Financial app UI moodboard." Dribbble, published Aug. 14, 2018 (Retrieved from the internet Jun. 15, 2020). Internet URL: <https://dribbble.com/shots/4955183> (Year: 2018).

Notification and Decision of Grant issued by the Japanese Patent Office in connection with Japanese Design Application No. 2018-028923 on Sep. 9, 2019.

Wang et al., Poster presentation: A comprehensive immunoscore to predict immunotherapy responses based on multivariate genomic/transcriptomic features, presented at the American Association for Cancer Research, Apr. 15, 2018, Chicago Illinois, abstract published online at the following URL: https://www.abstractsonline.com/pp8/#!/4562/presentation/2952.

Gibney, Geoffrey T., et al.; "Predictive biomarkers for checkpoint inhibitor-based immunotherapy"; Lancet Oncol. 2016; 17(12): e542-e551.

\* cited by examiner

| GROUP | FEATURE |
|---|---|
| ANTIGEN PRESENTATION | allMut |
| ANTIGEN PRESENTATION | nonSynMut |
| ANTIGEN PRESENTATION | B2M |
| ANTIGEN PRESENTATION | PSMB10 |
| ANTIGEN PRESENTATION | TAP1 |
| ANTIGEN PRESENTATION | TAP2 |
| ANTIGEN PRESENTATION | HLA-A |
| ANTIGEN PRESENTATION | HLA-B |
| ANTIGEN PRESENTATION | HLA-C |
| ANTIGEN PRESENTATION | HLA-DQA1 |
| ANTIGEN PRESENTATION | HLA-DRB1 |

| GROUP | FEATURE |
|---|---|
| T CELL/NK SIGNATURE | HLA-E |
| T CELL/NK SIGNATURE | NKG7 |
| T CELL/NK SIGNATURE | CMKLR1 |

| GROUP | FEATURE |
|---|---|
| CYTOLYTIC SIGNATURE | cd8_dec |
| CYTOLYTIC SIGNATURE | cd4_dec |
| CYTOLYTIC SIGNATURE | cd19_dec |
| CYTOLYTIC SIGNATURE | GZMA |
| CYTOLYTIC SIGNATURE | PRF1 |

| GROUP | FEATURE |
|---|---|
| CHECHPOINT | CTLA4 |
| CHECHPOINT | PD1 |
| CHECHPOINT | PDL1 |
| CHECHPOINT | PDL2 |
| CHECHPOINT | LAG3 |
| CHECHPOINT | TIGIT |
| CHECHPOINT | CD276 |

| GROUP | FEATURE |
|---|---|
| INTERFERON γ | CCL5 |
| INTERFERON γ | CD27 |
| INTERFERON γ | CXCL9 |
| INTERFERON γ | CXCR6 |
| INTERFERON γ | IDO1 |
| INTERFERON γ | STAT1 |

| GROUP | FEATURE |
|---|---|
| MDSC/TREG | CD15 |
| MDSC/TREG | CD25 |
| MDSC/TREG | CD33 |
| MDSC/TREG | CD39 |
| MDSC/TREG | CD11B |
| MDSC/TREG | FOXP3 |

FIG. 2

| GROUP | FEATURES | IMP. | CORR | 1FDB | PT5 INPUT | 1F.PRED |
|---|---|---|---|---|---|---|
| ANTIGEN PRESENTATION | HLA.B | 0.922 | △ | 0.615 | 0.212 | NO (R) |
| ANTIGEN PRESENTATION | all_tmb | 0.499 | △ | 0.269 | 0.865 | YES (G) |
| ANTIGEN PRESENTATION | HLA.A | 0.431 | △ | 0.154 | 0.712 | YES (G) |
| ANTIGEN PRESENTATION | HLA.C | 0.423 | △ | 0.423 | 0.596 | YES (G) |
| ANTIGEN PRESENTATION | nonSyn_tmb | 0.413 | △ | 0.346 | 0.865 | YES (G) |
| T CELL/NK SIGNATURE | HLA.E | 0.377 | △ | 0.846 | 0.404 | NO (R) |
| CHECKPOINT | PD1 | 0.338 | △ | 0.588 | 0.365 | NO (R) |
| ANTIGEN PRESENTATION | B2M | 0.337 | △ | 0.115 | 0.404 | YES (G) |
| ANTIGEN PRESENTATION | HLA.DRB1 | 0.321 | △ | 0.115 | 0.519 | YES (G) |
| CYTOLYTIC SIGNATURE | PRF1 | 0.370 | ▽ | 0.462 | 0.596 | NO (R) |
| CYTOLYTIC SIGNATURE | cd19_dec | 0.445 | ▽ | 0.692 | 0.788 | NO (R) |
| MDSC/TREG | CD25 | 0.470 | ▽ | 0.769 | 0.865 | NO (R) |
| INTERFERON γ | IDO1 | 0.489 | ▽ | 0.423 | 0.558 | NO (R) |
| INTERFERON γ | CXCR6 | 0.505 | ▽ | 0.500 | 0.558 | NO (R) |
| MDSC/TREG | CD15 | 0.586 | ▽ | 0.577 | 0.827 | NO (R) |
| FULL MODEL | | | | | | 5.5 |

FIG. 5

| FEATURES | CORRELATION | | IMPORTANCE | |
|---|---|---|---|---|
| | PD1 | CTLA4 | PD1 | CTLA4 |
| Antigen_processing_pathway | 0.314 | 0.445 | 0.445 | 0.482 |
| BM2 | 0.241 | 0.465 | 0.280 | 0.464 |
| HLA.A | 0.293 | 0.325 | 0.356 | 0.341 |
| HLA.B | 0.312 | 0.272 | 0.740 | 0.215 |
| HLA.C | 0.273 | 0.321 | 0.359 | 0.209 |
| HLA.DQA1 | 0.172 | 0.437 | 0.251 | 0.558 |
| HLA.DRB1 | 0.211 | 0.337 | 0.274 | 0.205 |
| PSMB10 | 0.148 | 0.272 | 0.190 | 0.196 |
| TAP1 | 0.126 | 0.424 | 0.236 | 0.416 |
| TAP2 | 0.151 | 0.424 | 0.250 | 0.300 |
| all_tmb | 0.242 | -0.079 | 0.426 | 0.187 |
| nonSyn_tmb | 0.175 | -0.080 | 0.361 | 0.190 |

| FEATURES | CORRELATION | | IMPORTANCE | |
|---|---|---|---|---|
| | PD1 | CTLA4 | PD1 | CTLA4 |
| T_cell_NK_signature | 0.189 | 0.345 | 0.447 | 0.428 |
| CMKLR1 | 0.002 | 0.283 | 0.168 | 0.172 |
| HLA.E | 0.194 | 0.373 | 0.325 | 0.318 |
| NKG7 | 0.012 | 0.323 | 0.176 | 0.189 |

| FEATURES | CORRELATION | | IMPORTANCE | |
|---|---|---|---|---|
| | PD1 | CTLA4 | PD1 | CTLA4 |
| Cytolytic_signature | -0.128 | 0.401 | 0.292 | 0.247 |
| GZMA | 0.005 | 0.379 | 0.238 | 0.361 |
| PRF1 | -0.081 | 0.402 | 0.315 | 0.273 |
| cd19_dec | -0.126 | 0.352 | 0.360 | 0.396 |
| cd14_dec | 0.127 | 0.171 | 0.257 | 0.209 |
| cd18_dec | -0.013 | 0.565 | 0.140 | 1.326 |

| FEATURES | CORRELATION | | IMPORTANCE | |
|---|---|---|---|---|
| | PD1 | CTLA4 | PD1 | CTLA4 |
| Checkpoint | -0.082 | 0.409 | 0.270 | 0.498 |
| CD276 | -0.014 | 0.046 | 0.202 | 0.357 |
| CTLA4 | -0.074 | 0.422 | 0.259 | 0.376 |
| LAG3 | -0.011 | 0.279 | 0.184 | 0.238 |
| PD1 | 0.002 | 0.306 | 0.289 | 0.177 |
| PDL1 | 0.121 | 0.142 | 0.226 | 0.199 |
| PDL2 | -0.022 | 0.321 | 0.224 | 0.228 |
| TIGIT | -0.023 | 0.363 | 0.198 | 0.395 |

| FEATURES | CORRELATION | | IMPORTANCE | |
|---|---|---|---|---|
| | PD1 | CTLA4 | PD1 | CTLA4 |
| Interferon_gamma | -0.054 | 0.387 | 0.214 | 0.380 |
| CCL5 | -0.068 | 0.388 | 0.204 | 0.272 |
| CD27 | 0.019 | 0.354 | 0.217 | 0.242 |
| CXCL9 | 0.066 | 0.243 | 0.135 | 0.205 |
| CXCR6 | -0.085 | 0.314 | 0.423 | 0.224 |
| IDO1 | -0.100 | 0.409 | 0.415 | 0.323 |
| STAT1 | 0.001 | 0.199 | 0.159 | 0.245 |

| FEATURES | CORRELATION | | IMPORTANCE | |
|---|---|---|---|---|
| | PD1 | CTLA4 | PD1 | CTLA4 |
| MDSC_Treg | -0.132 | 0.037 | 0.289 | 0.310 |
| CD11B | 0.016 | 0.050 | 0.205 | 0.253 |
| CD15 | -0.217 | 0.059 | 0.486 | 0.263 |
| CD25 | -0.033 | 0.139 | 0.391 | 0.257 |
| CD33 | 0.092 | 0.099 | 0.154 | 0.296 |
| CD39 | 0.040 | 0.102 | 0.259 | 0.124 |
| FOXP3 | 0.055 | 0.283 | 0.196 | 0.374 |

FIG. 7

METHOD FOR ADMINISTERING A CANCER TREATMENT

CROSS-REFERENCE TO RELATED APPLICATIONS

This application claims priority to U.S. Provisional Patent Application No. 62/593,802, filed Dec. 1, 2017, the entire contents of which are hereby incorporated herein.

BACKGROUND OF THE INVENTION

Detecting abnormal or cancerous cells in the body is an important task of the immune system. One mechanism involved is the immune checkpoint. For example, programmed cell death protein 1 (PD-1) and cytotoxic T-lymphocyte-associated protein 4 (CTLA-4) checkpoints on T-cells negatively regulate immune function and prevent overreaction (i.e., promote immune system self-recognition). However, this mechanism can be exploited by tumor cells to escape immune attacks. Immunotherapies such as PD-1 inhibition (e.g., anti-PD1 antibodies) and CTLA-4 (e.g., CTLA-4 antibodies) block check point activity, hence facilitating T-cell identification of disease or tumor cells as such.

However, although immune checkpoint therapies can be effective, responsiveness in all cancer patients is not guaranteed. Compared to traditional cancer therapies, immune checkpoint therapies have shown improvement of long term survival of patients with various cancers. However, only a subset of cancer patients responds to currently approved checkpoint inhibitor drugs including anti-CTLA-4 antibody (e.g., ipilimumab), and treatments targeting the PD-1 checkpoint pathway such as anti-PD-1 antibody (e.g., nivolumab) or anti-programmed death-ligand 1 (anti-PD-L1) antibody (e.g., atezolizumab). Therefore, it would be advantageous to be able to select patients who would respond to particular checkpoint therapies, and to predict which checkpoint target permits the best outcome in a given patient.

Many different genomic and cellular features may contribute to the effectiveness of immunotherapy for a given individual. A higher tumor mutation burden (TMB), for example, may positively affect response rate by increasing antigens presented on tumor cells, resulting in increased recognition by T-cells when PD-1 is blocked. CD4/CD8/CD19-expressing leukocyte tumor infiltration correlates with better clinical outcome since such cells help immunological attack of tumor cells and subsequent antigen release. Myeloid derived suppression cells and regulatory T cells (Tregs) sequestrate T-cell availability and correlate with worse survival in various patients. Since they are detectable and derivable features from next generation sequencing (NGS) data that interplay with each other, it is important to build a machine learning application that interrogate their relationship to immunotherapy responses and produces a prediction of responsiveness to therapy, such as checkpoint inhibition, or other cancer treatment, incorporating the context of many features acting in concert in a given individual based on responsiveness of others in view of their individual multifactorial contexts.

Furthermore, given the potentially large number of interacting genomic, cellular, and other features that may interact to determine whether a given individual will respond positively to checkpoint inhibition, an improved method of reporting responsiveness prediction is needed. For example, many different features may combinatorially interact in predicting responsiveness. When a machine learning method is applied to assess whether a patient may be more or less responsive to a given checkpoint inhibition, some features may be determined to have greater or lesser importance than others, different features may differ from various degrees from a level that suggests each may influence responsiveness, and different factors may signal a patient's greater or lesser responsiveness to different checkpoint inhibition treatments, in different individuals. Thus, a contextual report of a given patient's responsiveness including identification of features with significance in predicting responsiveness and the directionality in their effect of the prediction is required. However, given limited space for presentation of all such potential aspects of a prediction report, current reporting methods are insufficient. Thus, a new method for reporting a multitude of elements of a responsiveness prediction related is desired.

The present disclosure is directed to overcoming these and other deficiencies in the art.

SUMMARY OF THE INVENTION

In an aspect, disclosed is a computer-implemented method, including inputting to a trained machine learning classifier genomic information of a non-training subject, the genomic information of the non-training subject comprising features from a tumor profile obtained from the non-training subject, wherein the trained machine learning classifier trained on genomic information of a plurality of training subjects and a responsiveness of each of the plurality of training subjects to a treatment including a checkpoint inhibition, the genomic information of the plurality of training subjects comprising features of tumor samples obtained from each of a plurality of training subjects, wherein the machine-learning classifier trained to predict responsiveness to the treatment; generating a checkpoint inhibition responsiveness classification for the non-training subject using the trained machine-learning classifier, the checkpoint inhibition responsiveness classification predictive of the non-training subject responding to the checkpoint inhibition; and reporting the checkpoint inhibition responsiveness classification of the non-training subject using a graphical user interface. In an example, at least some of the features from a tumor profile obtained from the non-training subject or at least some of the features from a tumor profile obtained from one or more of the training subjects are selected from the following group of features: total mutational burden consisting of all mutations, total mutational burden consisting of non-synonymous mutations, beta 2 microglobulin (B2M) expression, proteasome subunit beta 10 (PSMB10) expression, antigen peptide transmitter 1 (TAP1) expression, antigen peptide transporter 2 (TAP2) expression, human leukocyte antigen A (HLA-A) expression, major histocompatibility complex class I B (HLA-B) expression, major histocompatibility complex class I C (HLA-C) expression, major histocompatibility complex class II DQ alpha 1 (HLA-DQA1) expression, HLA class II histocompatibility antigen DRB1 beta chain (HLA-DRB1) expression, HLA class I histocompatibility antigen alpha chain E (HLA-E) expression, natural killer cell granule protein 7 (NKG7) expression, chemokine like receptor 1 (CMKLR1) expression, tumor infiltration by cells expressing cluster of differentiation 8 (CD8), tumor infiltration by cells expressing cluster of differentiation 4 (CD4), tumor infiltration by cells expressing cluster of differentiation 19 (CD19), granzyme A (GZMA) expression, perforin-1 (PRF1) expression, cytotoxic T-lymphocyte-associated protein 4 (CTLA4) expression, programmed cell death protein 1 (PD1) expression, programmed death-ligand 1 (PDL1) expression, programmed cell death 1 ligand 2 (PDL2) expression, lymphocyte-activation gene 3 (LAG3) expression, T cell immunoreceptor with Ig and ITIM domains (TIGIT) expression, cluster of differentiation 276 (CD276) expression, chemokine (C-C motif) ligand 5 (CCL5), CD27 expression, chemokine (C-X-C motif) ligand 9 (CXCL9) expression, C-X-C motif chemokine receptor 6 (CXCR6), indoleamine 2,3-dioxygenase (IDO) expression, signal transducer and activator of transcription 1 (STAT1) expression, 3-fucosyl-N-acetyl-lactosamine (CD15) expression, interleukin-2 receptor alpha chain (CD25) expression, siglec-3 (CD33), cluster of differentiation 39 (CD39) expression, cluster of differentiation (CD118) expression, forkhead box P3 (FOXP3) expression, and any combination of two or more of the foregoing.

In another example, at least some of the training features or at least some of the non-training features include gene sets. In a further example, the gene sets were selected using single sample gene set enrichment analysis. In yet another example, the machine learning classifier is random forest. In a still further example, at least 50,000 trees are used in training the machine learning classifier. In yet a further example, the checkpoint inhibition responsiveness classification includes a prediction score and one or more feature identifiers, and the one or more feature identifiers are selected from the group consisting of a feature valence, a feature importance, and a feature weight.

In another example, the graphical user interface reports feature identifiers as aspects of an annulus sector, wherein an angle of the annulus sector reports the feature importance, an outer radius of the annulus sector reports the feature weight, and a color of the annulus sector reports the feature valence. In a further example, feature importance of a feature includes a Gini index decrease of the feature. In still another example, the graphical user interface reports an identifier of a feature if and only if the feature importance of the feature is above a threshold. In yet another example, the feature importance of the feature is not above the threshold if the square of the feature importance of the feature is not above 0.1. In still a further example, each of the annulus sectors includes an inner arc and the inner arcs of the annulus sectors are arranged to form a circle.

Another example further includes inputting to the trained machine learning classifier a responsiveness of the non-training subject to the treatment and further training the machine learning classifier, wherein further training includes training the trained machine learning classifier on features of tumor samples obtained from the non-training subject and a responsiveness of the non-training subject to the treatment. Yet another example further includes selecting a treatment based upon the generated checkpoint inhibition responsiveness classification.

In another aspect, disclosed is a computer system, including one or more microprocessors and one or more memories for storing a trained machine learning classifier and genomic information of a non-training subject, wherein the trained machine learning classifier trained on genomic information of a plurality of training subjects and a responsiveness of each of the plurality of training subjects to a treatment comprising a checkpoint inhibition, the genomic information of the plurality of training subjects comprising features of tumor profiles obtained from each of the plurality of training subjects, and the machine-learning classifier trained to predict responsiveness to the treatment, and the genomic information of the non-training subject comprising features from a tumor profile obtained from the non-training subject, and the one or more memories storing instructions that, when executed by the one or more microprocessors, cause the computer system to generate a checkpoint inhibition responsiveness classification for the non-training subject using the trained machine-learning classifier and report the checkpoint inhibition responsiveness classification of the non-training subject using a graphical user interface, the checkpoint inhibition responsiveness classification predictive of the non-training subject responding to the checkpoint inhibition.

In an example, at least some of the features from a tumor profile obtained from the non-training subject or at least some of the features from a tumor profile obtained from one or more of the training subjects are selected from the following group: total mutational burden consisting of all mutations, total mutational burden consisting of nonsynonymous mutations, beta 2 microglobulin (B2M) expression, proteasome subunit beta 10 (PSMB10) expression, antigen peptide transmitter 1 (TAP1) expression, antigen peptide transporter 2 (TAP2) expression, human leukocyte antigen A (HLA-A) expression, major histocompatibility complex class I B (HLA-B) expression, major histocompatibility complex class I C (HLA-C) expression, major histocompatibility complex class II DQ alpha 1 (HLA-DQA1) expression, HLA class II histocompatibility antigen DRB1 beta chain (HLA-DRB1) expression, HLA class I histocompatibility antigen alpha chain E (HLA-E) expression, natural killer cell granule protein 7 (NKG7) expression, chemokine like receptor 1 (CMKLR1) expression, tumor infiltration by cells expressing cluster of differentiation 8 (CD8), tumor infiltration by cells expressing cluster of differentiation 4 (CD4), tumor infiltration by cells expressing cluster of differentiation 19 (CD19), granzyme A (GZMA) expression, perforin-1 (PRF1) expression, cytotoxic T-lymphocyte-associated protein 4 (CTLA4) expression, programmed cell death protein 1 (PD1) expression, programmed death-ligand 1 (PDL1) expression, programmed cell death 1 ligand 2 (PDL2) expression, lymphocyte-activation gene 3 (LAG3) expression, T cell immunoreceptor with Ig and ITIM domains (TIGIT) expression, cluster of differentiation 276 (CD276) expression, chemokine (C-C motif) ligand 5 (CCL5), CD27 expression, chemokine (C-X-C motif) ligand 9 (CXCL9) expression, C-X-C motif chemokine receptor 6 (CXCR6), indoleamine 2,3-dioxygenase (IDO) expression, signal transducer and activator of transcription 1 (STAT1) expression, 3-fucosyl-N-acetyl-lactosamine (CD15) expression, interleukin-2 receptor alpha chain (CD25) expression, siglec-3 (CD33), cluster of differentiation 39 (CD39) expression, cluster of differentiation (CD118) expression, forkhead box P3 (FOXP3) expression, and any combination of two or more of the foregoing.

In another example, at least some of the training features or at least some of the non-training features include gene sets. In yet another example, the gene sets were selected using single sample gene set enrichment analysis. In still another example, the machine learning classifier is random forest. In a further example, at least 50,000 trees are used in training the machine learning classifier. In yet a further example, the checkpoint inhibition responsiveness classification comprises a prediction score and one or more feature identifiers, and the one or more feature identifiers are selected from the group consisting of a feature valence, a feature importance, and a feature weight. the instructions, when executed by the one or more microprocessors, cause the graphical user interface to report feature identifiers as aspects of an annulus sector, wherein an angle of the annulus sector reports the feature importance, an outer radius of the annulus sector reports the feature weight, and a color of the annulus sector reports the feature valence.

In another example, feature importance of a feature comprises a Gini index decrease of the feature. In yet another example, the instructions, when executed by the one or more microprocessors, cause the graphical user interface to report an identifier of a feature if and only if the feature importance of the feature is above a threshold. In yet a further example, the feature importance of the feature is not above the threshold if the square of the feature importance of the feature is not above 0.1. In still another example, the instructions, when executed by the one or more microprocessors, cause the graphical user interface to report an inner arc of each of the annulus sectors and a circle comprising the inner arcs of the annulus sectors. In still a further example, the instructions, when executed by the one or more microprocessors, cause the computer system to further train the machine learning classifier, wherein further training includes training the trained machine learning classifier on features of tumor samples obtained from the non-training subject and a responsiveness of the non-training subject to the treatment.

In yet another aspect, disclosed is a machine learning-based classifier for classification of immune checkpoint responsiveness, the machine learning-based classifier including a machine learning-based classifier, running on numerous processors, trained to predict responsiveness of a non-training subject to an immune checkpoint inhibition treatment, wherein the machine learning-based classifier trained by inputting, to the machine-learning based classifier, genomic information of a plurality of training subjects and a responsiveness of each of the plurality of training subjects to the treatment, the genomic information of the plurality of training subjects comprising features of tumor profiles obtained from each of the plurality of training subjects, an input processor that inputs features of tumor samples obtained from the non-training subject into the machine learning-based classifier, wherein the machine-learning classifier is configured to generate a checkpoint inhibition responsiveness classification for the non-training subject, the checkpoint inhibition responsiveness classification predictive of the subject responding to checkpoint inhibition treatment; and an output processor that reports checkpoint inhibition responsiveness classification. In an example, the checkpoint inhibition responsiveness classification includes a prediction score and a plurality of identifiers.

BRIEF DESCRIPTION OF THE DRAWINGS

These and other features, aspects, and advantages of the present disclosure will become better understood when the following detailed description is read with reference to the accompanying drawings, wherein:

FIG. 2 shows some non-limiting examples of features that may be relevant in training a classifier and predicting a patient's responsiveness to treatment in accordance with aspects of the present disclosure.

FIG. 5 is an example of a method of reporting a subject's responsiveness to a treatment as predicted by a trained machine learning-based classifier in accordance with aspects of the present disclosure.

FIG. 7 is an example of a method of reporting and comparing a subject's responsiveness to different treatments as predicted by a trained machine learning-based classifier in accordance with aspects of the present disclosure.

DETAILED DESCRIPTION OF THE INVENTION

Figure 1:
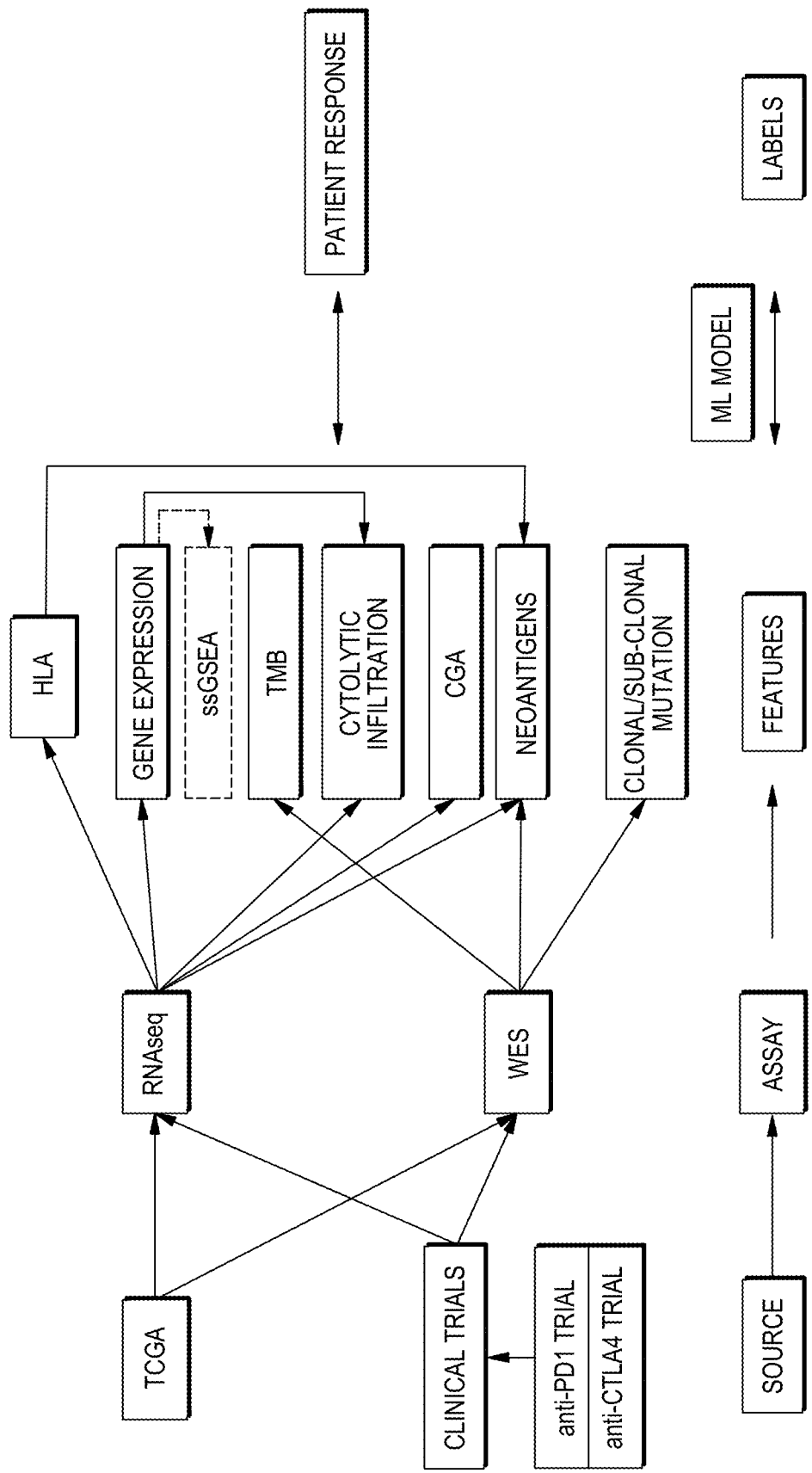
FIG. 1 is a web diagram showing options for performing a method in accordance with aspects of the present disclosure.

This disclosure relates to a machine learning method for obtaining a prediction of whether an individual may respond to treatment with a checkpoint inhibitor or other cancer treatment. Different individuals may or may not respond to a given treatment. Responsivity to a treatment may depend not simply on the presence or absence of a given feature or quantitative amount of a given feature in isolation. Rather, a number of features may combine differentially between individuals to render some individuals more likely to responds to a given treatment and other individuals less so. Standard methods of predicting patient responsiveness on the basis of a single feature, or even several features, do not accurately predict responsiveness under circumstances where a large number of factors, which may very independently of each other, act in concert in this way.

A machine learning method presents a novel solution to this shortcoming of prevailing diagnostic prediction methods. In supervised machine learning, for example, large data sets representing many individuals' numerous features, paired with each individual's known responsiveness to a given treatment, may be loaded onto computer memory storage. The storage medium of the computer contains instructions that instruct the computer processor to process individuals' feature information and responsiveness to identify patterns in feature information that signal a high or low likelihood of an individual being responsive to the given treatment. An advantage of using a machine learning method for such an analysis is that it permits identification of patterns in features and their relevance to predicting responsiveness to treatment that are not possible without the high data storage and retrieval capabilities of computer systems and their ability to process high amounts of information. A computer-implemented machine learning system may process tens or hundreds of features or more of tens or hundreds of subjects or more to identify patterns of features and their aggregate correlations to the individuals' responsiveness. Patterns so identified may be otherwise undetectable, requiring as they do the processing of large amounts of data in complex sets of information.

To determine features of an individual, a tissue sample of the individual, such as an individual with cancer, may be obtained and characteristics of such tissue determined. In some examples, obtained tissue may be a sample of cells taken from a tumor. In other examples, obtained tissue may be non-tumor tissue obtained from the individual.

Here, checkpoint inhibition refers to treatments that block a process by which tumor cells activate self-recognition pathways in the immune system and thereby prevent immune cell attack and cytolysis of tumor cells. Activation of such pathways by tumor cells is thought to contribute to the refractoriness of some patients to immuno-oncology treatments, such as where immune cells are engineered to recognize and target tumor cells. Examples of checkpoint inhibition include the CTLA4 pathway. CTLA4 is a protein receptor expressed on regulatory T cells. It may also be expressed on conventional T cells following activation thereof, as is often seen in cancer. When CTLA4 binds CD80 or CD87, proteins expressed on the surface of antigen-presenting cells, immunosuppression results. In healthy cells this mechanism promotes self-recognition and prevents immunological attack of self-cells. However, in cancer, upregulation of this pathway helps tumor cells evade detection and attack by the immune system. Examples of checkpoint inhibitor treatments that inhibit this pathway (such as the anti-CTLA4-antibody ipilimumab) may promote the ability of the immune system to target and destroy tumor cells, such as when paired with other immuno-oncological treatments that stimulate anti-tumor immunoresponsiveness.

Similarly, another example of checkpoint inhibition is the PD-1 pathway. Binding of PD-1 on T cells by the PD1-L1 receptor expressed on self-cells causes an immunosuppressive response. As with the CTLA4 pathway, this pathway is also utilized by tumor cells to evade detection and attack by the immune system. Examples of checkpoint inhibitor treatments that inhibit this pathway (such as the anti-PD-1 antibodies pembrolizumab, nivolumab, and cemiplimab and the anti-PD-L1 antibodies atezolizumab, avelumab, and durvalumab) may promote the ability of the immune system to target and destroy tumor cells, such as when paired with other immuno-oncological treatments that stimulate anti-tumor immunoresponsiveness.

As used herein, the term checkpoint inhibitor or checkpoint inhibition treatment or the like includes these treatments as well as other treatments that inhibit checkpoint inhibitor pathways, including treatment with other antibodies or pharmaceutical compounds that function by preventing CTLA4 or PD-1 interaction with their cognate ligands or receptors or activation of their downstream signaling sequelae or cellular functions.

Many features may be relevant in producing a prediction of whether individuals' responsiveness to a given treatment. Examples may include genetic sequence information contained in the genome of cells taken from an individual, genetic sequence information expressed in RNA transcribed from the genome of an individual's cell, amounts of expression of transcripts of genomic sequences which may be reflected in amounts of a corresponding RNA transcript or protein product thereof in a sample, or types of cells present in a sample. In an example where a sample includes tumor tissue or cells from an individual, such information may indicate characteristics of tumor cells, i.e. cells with a modified genomic sequence or sequences compared to the general population or non-tumor cells of the individual or a reference genome referred to in a genetic sequencing paradigm. Tumorigenesis may result from a change in the nucleotide sequence or more than one change and/or of more than one sequence in genomic DNA. In some cases, for example, an accumulation of multiple such sequence modifications may together function to convert a cell from a non-diseased cell to a tumor cell. In other cases, an initial accumulation of one or several such modifications in a cell may predispose the cell to accumulating further such modifications. In still other cases, a proliferation of such modifications in a cell may signify not that any particular modifications directly participate in or are responsible for development of a tumor. Rather, a tumorigenic process may result in some modifications that directly induce transformation of a cell into a tumor cell, but may also create other modifications that do not.

Thus, some individuals' tumor cells may have a large number of such modifications to sequences of genomic DNA, whereas other individuals' may have fewer. Of those, some may result in transcripts or protein products with amino acid sequences altered as a result of the genomic modification, such as where a modification of DNA sequence in genomic DNA results in production of a protein or RNA molecule having a sequence that differs from that which would have been produced had the modification not occurred. Such a modifications are referred to as non-synonymous mutations. Other modifications may be of non-coding DNA, or may be modifications of coding DNA that do not alter protein amino acid sequences. For example, modifications to intronic sequences or non-transcribed DNA may not result in protein products whose amino acid sequence differs from that of proteins produced from a genome not carrying the same modification. Such modifications are referred to as synonymous mutations. Thus, different tumors may contain different total numbers of modifications to genomic DNA, including different total numbers of non-synonymous mutations, different numbers of synonymous mutations, or different numbers of both (or the same total number of genomic mutations but different numbers of synonymous mutations and different numbers of non-synonymous mutations). The number of mutations a cell carries is referred to as its mutational burden or total mutational burden, whereas the total number of non-synonymous mutations it carries is referred to as its non-synonymous mutational burden and the number of synonymous mutations it carries is referred to as its synonymous mutational burden.

The conversion of a cell from a non-tumor cell to a tumor cell may correspond to an accumulation of such modifications to genomic DNA. Such accumulation may be an accumulation of synonymous mutations, of non-synonymous mutations, or of both types. Either way, total mutational burden may increase leading up to, upon, and following conversion from a non-tumor cell to a tumor cell. Furthermore, a tumor cell's mutational burden may influence whether a checkpoint inhibitor is likely to be effective in stimulating an anti-tumor response by the immune system. The more mutations a tumor cell carries, the greater chance that suppressing checkpoint inhibition may disinhibit the immune system from recognizing it as a diseased cell and attacking it. In particular, non-synonymous tumor mutational burden may be positively correlated with the ability of checkpoint inhibition to disinhibit an antitumor immune response. Proteins with mutated amino acid sequences, produced consequential to non-synonymous mutations, can be identified in cells as abnormal and presented on cell membranes as a signal of a disease state occurring within the cell. For example, tumors may express proteins with mutated amino acid sequences, referred to as neoantigens. Tumor cells expressing such neoantigens may express mutated fragments of such neoantigens on their cell membranes.

Such neoantigen presentation may stimulate recognition by the immune system that the cell is diseased (e.g., a tumor cell) and promote targeted destruction of such cells by the immune system. A countervailing process in tumors, however, may use the checkpoint pathway to evade immune detection. Thus, whether a checkpoint inhibitor may assist in enhancing immuno-oncological treatment may depend on a tumor's mutational burden. A higher burden may correspond to a higher level of neoantigen presentation, increasing the chances of stimulated antitumor immunogenicity when checkpoint inhibition treatment is given. A higher total mutational burden may signify greater neoantigen expression, in that on average a higher total mutational burden may signify a higher non-synonymous mutational burden. Furthermore, a higher non-synonymous tumor mutational burden may also signify greater neoantigen expression and thus a higher likelihood that checkpoint inhibition would be effective. It is also possible that synonymous tumor mutational burden may be correlated with responsiveness to checkpoint inhibition, and/or that some combination of synonymous and non-synonymous tumor mutational burden, such as may be reflected in total mutational burden, may correlate with responsiveness to checkpoint inhibition. Thus, total mutational burden, non-synonymous tumor mutational burden, synonymous tumor mutational burden, or any combination of two or more thereof, may be predictive of checkpoint responsiveness, and may be a feature or features included in a machine learning method as disclosed herein.

Aside from or in addition to whether a mutation is synonymous or non-synonymous, other or additional characteristics of a mutation may also be present and the number or type thereof, as with whether a mutation or mutations are synonymous or non-synonymous, may be relevant in predicting responsiveness to treatment. For example, some mutations, referred to as nonstop mutations, are mutations within a stop codon that result in production of an RNA product translation of which continues past where in would otherwise stop due to the mutated portion of the RNA transcript. Another form of mutation is a frame shift mutation, which includes an insertion (frame shift insertion) or deletion (frame shift deletion) of a number of contiguous nucleotides that is not divisible by three (for example, a single nucleotide insertion or deletion), leading to a shifting of the read sequence of codons thus resulting in recruitment of different tRNA molecules during translation of the resulting RNA transcript and thus altered amino acid sequences of translated protein. Other mutations may be splice site mutations, which occur at or near splice sites thus modifying normal mRNA splicing and resulting in modified RNA transcripts. Or a mutation may be a missense mutation, in which a single nucleotide is changed such that a codon in which it contains is altered so as to recruit a different species of tRNA during translation and thus production of a protein with a different amino acid sequence.

Another possible mutation may be a start mutation, which is a mutation to a transcriptional start site or to a start codon, leading to changes in where transcription or translation begins, respectively. For example, a start site mutation may prevent initiation of transcription from that start site. Or, a mutation could create a transcriptional start site that was not previously present. A transcriptional start site mutation may lead to transcription of an RNA transcript that, though of a different length than would otherwise have been produced, is in-frame with such transcript produced in the absence of the mutation, or that may be out of frame therewith. Analogous mutations to a start codon may also occur, leading to transcription of an RNA product from which initiation of translation does not occur, or where initiation of translation occurs from which it would not previously have been initiated. Such stop codon mutations may be in-frame or out of frame as well. Or, a mutation may be a nonsense mutation, i.e., a mutation that leads to an RNA transcript with a premature stop codon. Any of the foregoing mutations may be a single nucleotide polymorphism (SNP). Any one or more of the foregoing types of mutations may be features with relevance to predicting an individual's responsiveness to a given treatment, such as with a given checkpoint inhibitor.

In another example, an amount of infiltration of a tumor by lymphocytes may be predictive of responsiveness to a checkpoint inhibitor. Tumors contain not only cells that have transformed from non-tumor into tumor cells but also other, non-transformed cells. Examples include cells of the immune system that do or may play a role in stimulating an immune response against transformed cells within the tumor. Immune cells, in particular lymphocytes, that are comingled with transformed cells in a tumor are referred to a tumor infiltrating lymphocytes. Levels of tumor infiltrating lymphocytes, and tumor infiltrating lymphocytes expressing different markers that serve as identifiers of lymphocyte phenotype, may be predictive of whether a subject from which a tumor sample was taken will be responsive to checkpoint inhibition. Because a tumor is a heterogeneous mixture of, for example, tumor cells and tumor infiltrating lymphocytes, it may be advantageous to distinguish lymphocyte marker expression on tumor infiltrating lymphocytes present in the sample ant lymphocyte markers potentially expressed on other cells within the tumor sample such as transformed tumor cells.

For example, tumor infiltrating lymphocytes may express transcripts (e.g., RNA) of genes encoding cluster of differentiation 8 (CD8), cluster of differentiation 4 (CD4), or cluster of differentiation 19 (CD19), each of which may serve as a marker of lymphocyte phenotype when expressed in a cell. Thus, levels of expression of CD8, CD4, CD19, or any combination of any two or more of the foregoing, may be determined from a tumor sample. For example, amount of RNA therefore may be determined from the sample. Because such determination may reflect not only expression thereof by tumor infiltrating lymphocytes but also be other cells within the tumor sample such as transformed tumor cells, it may be advantageous to determine how much of the detected amount of expression thereof is attributable to expression by tumor infiltrating lymphocytes and how much is not. In order to do so, a process of deconvolution may be applied, whereby a level of expression by tumor infiltrating lymphocytes may be determined as opposed to expression by other cells. Various options for performing tumor infiltrating lymphocyte deconvolution are available, including as described in, for example, Gaujoux et al. (2013) CellMix: a comprehensive toolbox for gene expression deconvolution.

Bioinformatics 29:2211-2212, and Finotello et al. (2018), Quantifying tumor-infiltrating immune cells from transcriptomics data, Cancer Immunology, Immunotherapy 67:1031-1040. Deconvolution analysis may be performed in, as a non-limiting example, R programming language.

In particular, by a process referred to as tumor infiltrating lymphocyte deconvolution, the level of expression of a given lymphocyte transcript (e.g., CD8, CD4, or CD19) can be used to determine what percentage of lymphocyte cells in a tumor sample are CD4-expressing or CD8 expressing or CD19 expressing. That is, more than merely signifying the amount of lymphocyte infiltration of a tumor as represented by the amount of a given lymphocyte transcript that may be identified in a tumor, tumor infiltrating lymphocyte deconvolution can further provide an indication of which type of lymphocyte, identified by species of transcript expressed, accounts for what percentage of overall infiltration of the tumor. Total amount of lymphocyte infiltration of a tumor may be relevant in predicting whether an individual will be responsive to a given treatment such as a checkpoint inhibitor, and the specific contribution of lymphocyte infiltration of the tumor made by lymphocytes expressing a given transcript (for example, but not limited to, CD4 or CD8 or CD19) may also be relevant in making such a prediction.

Various other features may be relevant in predicting whether an individual will be responsive to checkpoint inhibition. Such features may be generally classified according to processes theoretically related to whether a checkpoint inhibitor may or may not be effective in promoting or enhancing an onco-immunological response. For example, some features may relate to whether and to what degree tumor cells may be more or less likely to express antigens of mutated proteins on their cell surfaces and thereby increase the chances of an anti-tumor immune response. Examples of such features already discussed include types of tumor mutational burden, such as total tumor mutational burden or non-synonymous tumor mutational burden, for example. Other examples include expression levels of different proteins or transcripts of genes encoding proteins known to be involved in antigen presentation for stimulation of an immune response. Some non-limiting examples include beta 2 microglobulin (B2M), proteasome subunit beta 10 (PSMB10), antigen peptide transmitter 1 (TAP1), antigen peptide transporter 2 (TAP2), human leukocyte antigen A (HLA-A), major histocompatibility complex class I B (HLA-B) expression, major histocompatibility complex class I C (HLA-C), major histocompatibility complex class II DQ alpha 1 (HLA-DQA1), and HLA class II histocompatibility antigen DRB1 beta chain (HLA-DRB1). These gene products are known to play various steps in the presentation of protein fragments, or antigens, or a cell's surface and recognition by immune T cells.

Levels of expression of any one, or any combination of two or more, or any of these gene products in a tumor could indicate levels of antigen expression on the surface of tumor cells. For example, expression of such products may influence the degree of presentation of protein products of genomic DNA bearing a non-synonymous mutation on a cell's surface. Where expression increases antigen presentation, likelihood of presenting mutated antigens that T cells are likely to recognize as signifying a diseased cell and consequently trigger an anti-tumor immune response may increase the chances that a given checkpoint inhibitor may be effective in producing a response in a subject. Thus, where expression level of any or combination of two or more of the foregoing is positively or negatively correlated with degree of antigen presentation on cells within a tumor sample, such expression level may be positively or negatively correlated, respectively, with likelihood that the subject from which the tumor was samples would respond to a given checkpoint inhibitor.

Another type of feature may include level of expression of T cells or NK cells present in a tumor sample taken from a subject and which may also be relevant to a prediction of responsiveness to a treatment such as checkpoint inhibition. For example, level of expression of HLA class I histocompatibility antigen alpha chain E (HLA-E), natural killer cell granule protein 7 (NKG7), chemokine like receptor 1 (CMKLR1), or any combination of two or more thereof, may also be predictive of response to a checkpoint inhibitor. Thus, a feature may include a measure of expression of one or more of these products or RNA transcripts therefore.

Another type of feature may relate to presence or levels of expression of proteins or transcripts therefor that are related to or indicative of enhanced cytolytic activity such as may be promoted by an anti-tumor immune response, or which may inhibit such activity. Tumor infiltrating lymphocyte deconvolution measures discussed above may be examples of such features (for example, deconvolution of tumor infiltration by cells expressing cluster of differentiation 8 (CD8), cluster of differentiation 4 (CD4), or cluster of differentiation 19 (CD19)). Other non-limiting examples of this category of feature may include levels of expression of granzyme A (GZMA) or perforin-1 (PRF1) or any combination of two or more of the foregoing, or RNA transcripts therefor.

Still other features may be related to processes or functions in checkpoint inhibition of anti-tumor immune responsiveness. Levels of expression of various protein products or transcripts therefor of players in checkpoint inhibition within a tumor sample from a subject may be relevant in predicting whether the subject will respond to treatment with a cancer therapy such as a checkpoint inhibition treatment. Examples of such features may include expression of, or of RNA transcripts for, cytotoxic T-lymphocyte-associated protein 4 (CTLA4), programmed cell death protein 1 (PD1), programmed death-ligand 1 (PDL1), programmed cell death 1 ligand 2 (PDL2), lymphocyte-activation gene 3 (LAG3), T cell immunoreceptor with Ig and ITIM domains (TIGIT), cluster of differentiation 276 (CD276), or any two or more of the foregoing.

Other features that may be relevant in predicting whether an individual will respond to treatment include expression of proteins, or RNA transcripts therefor, related to interferon γ activity such as products whose expression is downstream of interferon γ release and activity at a receptor therefore. Examples of this type of feature may include expression of, or expression of RNA transcripts for, chemokine (C-C motif) ligand 5 (CCL5), CD27, chemokine (C-X-C motif) ligand 9 (CXCL9), C-X-C motif chemokine receptor 6 (CXCR6), indoleamine 2,3-dioxygenase (IDO), signal transducer and activator of transcription 1 (STAT1), or any combination of two or more of the foregoing. Other indicators of interferon γ activity may also be predictive of responsiveness to treatment such as checkpoint inhibition.

Other features that may be relevant in predicting whether an individual will respond to treatment include expression of proteins, or RNA transcripts therefor, related to myeloid-derived suppressor cells (MDSC) or regulatory T cells (Treg), which may confer immunosuppressive effects on anti-tumor immune responsiveness and may blunt or prevent effectiveness of immuno-oncology treatments. Examples of such features may include expression from a tumor sample from a subject tumor 3-fucosyl-N-acetyl-lactosamine (CD15), interleukin-2 receptor alpha chain (CD25), siglec-3 (CD33), cluster of differentiation 39 (CD39), cluster of differentiation (CD118) expression, forkhead box P3 (FOXP3), or any combination of two or more of the foregoing. Tumor expression levels of other species of protein or corresponding RNA transcripts indicative of presence of such cells or their activity may also be relevant to whether an individual will respond to checkpoint inhibitor treatment or other therapies for cancer.

Any one or more of any of the foregoing features may be relevant, to different degrees, to making a prediction as to whether an individual will respond to treatment with a given cancer treatment, including treatment with a checkpoint inhibitor. Any of the features may relate to or embody genomic information regarding the subject's tumor which was samples and tested for determination of the feature. In this case, the term genomic is used to include not only information related to the sequence of nucleotides in genomic DNA (such as, for example, features related to mutational burden). Here, genomic information represented by feature measures also includes measures of levels of expression of various products of genome transcription or protein products produced from such transcripts. Thus, levels of expression of any of the different protein products described above, or other protein products involved in similar pathways as those specifically identified, or levels of expression of RNA transcripts therefore, may be included in genomic information as it relates to predictive features as disclosed herein. Also included in genomic information related to features may be measures of tumor infiltrating lymphocyte deconvolution features.

In addition to measures of individual features, patterns of correlated expression levels of features known or believed to be related to a given pathway or function or cell type may also be features with relevance to responsiveness to checkpoint inhibition or other cancer treatment. For example, of the foregoing features, groups of some sharing commonalities of pathways or cellular or physiological responsiveness or indications of cellular phenotype may be identified and a determination made based on measurement of the individual features whether they, as a group, are coordinately up-regulated or down-regulated or more generally expressed or otherwise present as a group in a correlatedly high or low level in a sample from a given subject's tumor. In some examples, a measure of such generalized measurement of grouped features may itself be entered as a feature, in addition to individual features, for training a machine learning classifier, predicting a subject's responsiveness to checkpoint inhibition or other treatment, or both. Here, such groupings of features to obtain an additional feature to represent the expression level, etc., of the grouping as a whole is referred to as a gene set. Thus, a gene set may include a combinatorial measure representing a correlational indication of presence of genomic mutation, expression levels of particular RNA transcripts, presence of identified cell types, etc.

For a non-limiting example, of the foregoing features, some are related to antigen presentation, whereby cells such as tumors express protein fragments on their cell membrane for monitoring by the immune system. As described above, antigen presentation my increase likelihood of stimulating an anti-tumor immune response such as with a checkpoint inhibitor. Some examples of such features may include total mutational burden, non-synonymous mutational burden, or other mutational burden (nonstop mutational burden, frame shift mutational burden (insertional, deletional, or either), splice site mutational burden, missense mutational burden, start mutational burden, (in-frame, out-of-frame, or either), nonsense mutational burden, start codon mutational burden (including start codon SNP or other), in-frame insertion mutational burden, in-frame deletional mutational burden, or other SNP mutational burden, or any combination of two or more of the foregoing. Other non-limiting examples of features pertaining to antigen presentation may include beta 2 microglobulin (B2M), proteasome subunit beta 10 (PSMB10), antigen peptide transmitter 1 (TAP1), antigen peptide transporter 2 (TAP2), human leukocyte antigen A (HLA-A), major histocompatibility complex class I B (HLA-B) expression, major histocompatibility complex class I C (HLA-C), major histocompatibility complex class II DQ alpha 1 (HLA-DQA1), and HLA class II histocompatibility antigen DRB1 beta chain (HLA-DRB1). In addition to features related to presence or expression levels, etc., related to individual examples from among the foregoing features, an additional feature may represent a degree to which some or all of the foregoing are coordinately up- or down-regulated, or otherwise present in high or low levels in a subject's tumor (whether for machine learning classifier training or prediction).

As another non-limiting example, some features are related to level of expression of T cells or NK cells present in a tumor sample taken from a subject and which may also be relevant to a prediction of responsiveness to a treatment such as checkpoint inhibition. For example, level of expression of HLA class I histocompatibility antigen alpha chain E (HLA-E), natural killer cell granule protein 7 (NKG7), chemokine like receptor 1 (CMKLR1), or any combination of two or more thereof, may also be predictive of response to a checkpoint inhibitor. In addition to features related to presence or expression levels, etc., related to individual examples from among the foregoing features, an additional feature may represent a degree to which some or all of the foregoing are coordinately up- or down-regulated, or otherwise present in high or low levels in a subject's tumor (whether for machine learning classifier training or prediction).

As another non-limiting example, some features are related to indicators of immunologically stimulated cytolysis, such as when an immune response promotes cell death and cell lysis such as of tumor cells, present in a tumor sample taken from a subject and which may also be relevant to a prediction of responsiveness to a treatment such as checkpoint inhibition. For example, deconvoluted CD8 expression, deconvoluted CD4 expression, deconvoluted CD19 expression (deconvolution representing proportional contribution CD8, CD4, or CD19-expressing cells represent, respectively, relative to the number of tumor infiltrating lymphocytes present in a tumor sample), levels of expression of granzyme A (GZMA) or perforin-1 (PRF1), or any combination of two or more of the foregoing, or RNA transcripts therefor, may also be predictive of response to a checkpoint inhibitor. In addition to features related to presence or expression levels, etc., related to individual examples from among the foregoing features, an additional feature may represent a degree to which some or all of the foregoing are coordinately up- or down-regulated, or otherwise present in high or low levels in a subject's tumor (whether for machine learning classifier training or prediction).

As another non-limiting example, some features are related to cellular and molecular processes involved in checkpoint inhibition functions present in a tumor sample taken from a subject and which may also be relevant to a prediction of responsiveness to a treatment such as checkpoint inhibition. Non-limiting examples of such features may include expression of, or of RNA transcripts for, cytotoxic T-lymphocyte-associated protein 4 (CTLA4), programmed cell death protein 1 (PD1), programmed death-ligand 1 (PDL1), programmed cell death 1 ligand 2 (PDL2), lymphocyte-activation gene 3 (LAG3), T cell immunoreceptor with Ig and ITIM domains (TIGIT), cluster of differentiation 276 (CD276), or any two or more of the foregoing. In addition to features related to presence or expression levels, etc., related to individual examples from among the foregoing features, an additional feature may represent a degree to which some or all of the foregoing are coordinately up- or down-regulated, or otherwise present in high or low levels in a subject's tumor (whether for machine learning classifier training or prediction).

As another non-limiting example, some features are related to indicators or cellular and molecular pathways participating in interferon γ activity present in a tumor sample taken from a subject and which may also be relevant to a prediction of responsiveness to a treatment such as checkpoint inhibition. Non-limiting examples of such features may include expression of, or expression of RNA transcripts for, chemokine (C-C motif) ligand 5 (CCL5), CD27, chemokine (C-X-C motif) ligand 9 (CXCL9), C-X-C motif chemokine receptor 6 (CXCR6), indoleamine 2,3-dioxygenase (IDO), signal transducer and activator of transcription 1 (STAT1), or any combination of two or more of the foregoing. In addition to features related to presence or expression levels, etc., related to individual examples from among the foregoing features, an additional feature may represent a degree to which some or all of the foregoing are coordinately up- or down-regulated, or otherwise present in high or low levels in a subject's tumor (whether for machine learning classifier training or prediction).

As another non-limiting example, some features are related to MDSC or Treg presence or activity present in a tumor sample taken from a subject and which may also be relevant to a prediction of responsiveness to a treatment such as checkpoint inhibition. Non-limiting examples of such features may include expression from a tumor sample from a subject tumor 3-fucosyl-N-acetyl-lactosamine (CD15), interleukin-2 receptor alpha chain (CD25), siglec-3 (CD33), cluster of differentiation 39 (CD39), cluster of differentiation (CD118) expression, forkhead box P3 (FOXP3), or any combination of two or more of the foregoing. In addition to features related to presence or expression levels, etc., related to individual examples from among the foregoing features, an additional feature may represent a degree to which some or all of the foregoing are coordinately up- or down-regulated, or otherwise present in high or low levels in a subject's tumor (whether for machine learning classifier training or prediction).

Thus, in some examples, one or more gene sets may be identified and a measure of the coordinate or correlated degree of up- or down-regulation in a subject's tumor of features related to such gene set may be provided as an additional feature for training a machine-learning classifier or predicting a subject's responsiveness to checkpoint inhibition or other treatment or both. Examples of gene sets include gene sets related to antigen presentation, signatures of T cell and NK cells, cytolysis indicators, checkpoint inhibition, interferon γ, and MSDC/Treg presence or activity. In some cases, one or more such gene set, together with one or more of any of the other individual features discussed above, may be included in training or a machine learning classifier its use in predicting a patient's responsiveness to checkpoint inhibition or other treatment. Various methods may be employed in ascertaining a generalized measure of how features within a gene set feature are coordinately up- or down-regulated or otherwise expressed or present at high or low levels coordinately or in a correlated manner. One example may include an analysis referred to as single sample gene set enrichment analysis (ssGSEA). ssGSEA uses an empirical cumulative distribution function to ascertain such grouped enrichment of a gene set, as described in, for example, Barbie et al. (2009), Systematic RNA interference reveals that oncogenic KRAS-driven cancers require TBK1, Nature 462:108-112. ssGSEA may be performed, as a non-limiting example, in R programming language.

For the foregoing features, some, or any combination of any two or more, may be used both for training a machine learning classifier as well as for using a trained machine learning classifier to predict whether a subject will or how likely the subject is to respond to treatment such as with a checkpoint inhibitor. It is not necessary that all of the foregoing features be used to train a machine learning classifier, however. A machine learning classifier may be trained by a set of features that includes all of the foregoing, or excludes any one or more of the foregoing. All combinations and permutations suggested by this optional inclusion and exclusion are hereby incorporated in their entirety though not necessarily explicitly recited verbatim. A skilled person would be capable of conceptualizing subsets, combinations, sub-combinations, and permutations possible with the foregoing features. Likewise, additional features may be included as well, whether in addition to all of the foregoing or merely combination, sub-combinations, permutations, or other mixes of fewer than all of the foregoing features. All such different examples are expressly included in the present disclosure.

In some examples, the features of any subject used to train the machine learning classifier are the same as the features used for any and all other subjects in training the machine learning classifier. However, in other examples, different features may be provided for different subject used to train the machine learning classifier. In other words, some subjects may have features included in their training set that are not included in features from the training sets of other subjects. Similarly, in some examples, to obtain from a machine learning classifier a prediction related to a subject's responsiveness to a treatment, features obtained from a tumor sample from the subject for obtaining the prediction may be the same as features used in training the classifier. That is, features from all subjects used to train the machine learning classifier may all be the same as each other's, and also the same as the subject for whom a prediction is sought from the machine learning classifier. In other examples, there may be a mismatch between trained subjects' features used to train a machine learning classifier and a subject for whom a prediction is sought from the machine learning classifier. Features from some or all subjects used to train the machine learning classifier may include features for which there are not corresponding features from the subject for whom a prediction is sought from the machine learning classifier.

In some examples, a subject for whom a prediction is sought from a machine learning classifier may lack a feature that corresponds to a feature from one or some or all subjects used to train the machine learning classifier. In other examples, the subject may have a similar feature but not an identical feature, and the similar feature may be used in place of the absent identical feature of the subject. For example, a machine learning classifier may have been trained on features that, for at least some training subjects, include one or more gene set features, such as may be obtained using ssGSEA as described above. For some of the training subjects for whom gene sets were used to train the machine learning classifier, some such sets may have been obtained from the same underlying individual features. For example, a gene set of antigen presentation-related gene set feature may have been obtained from the same underlying features for all subjects used for training the machine learning classifier. In other examples, some an antigen-presentation related gene set for one training subject may be based on underlying features that include some such features that were not included in ascertaining an antigen-presentation related gene set from another training subject. This may also be true for other gene sets. Furthermore, a gene set feature subject from whom a prediction is sought from a trained machine learning classifier may be used in obtaining the prediction, and the feature value for the gene set may have been obtained from an underlying set of individual features from the subject that does not include at least one or more underlying features that had been used in obtaining the corresponding gene set feature value for one or more of the training subjects and used in training the machine learning classifier.

Features may be ascertained by known methods of determining genetic sequencing data or levels of protein or RNA transcript expression in a biological sample. For example, the significant amount of nucleotide sequence information that can be obtained using next generation sequencing technologies may provide both genome-related features (e.g., total mutational burden, etc.) as well as levels of expression of, for example, RNA transcripts, depending on the type of next generation sequencing used to obtain a given feature. Examples of appropriate methods include whole genome sequencing, whole exome sequencing, whole transcriptome sequencing, mRNA sequencing, gene array analysis, RNA array analysis, protein analysis such as protein array, or other related methods for ascertaining presence or levels or amounts of features used to train and/or obtain a prediction from a machine learning classifier in accordance with aspects of the present disclosure. In some examples, the same set of techniques may be used for obtaining features from all training subjects for training the machine learning classifier, and from a subject for whom a prediction is sought. In other examples, there may be methodological differences between how a feature or some features were determined for different training subjects, and/or for how features used for obtaining a prediction were obtained for a subject for whom a prediction is sought.

In addition to training a machine learning classifier with features from training subjects, training subjects' responsiveness to a treatment is also loaded into a machine learning classifier. Thus, a training subject is a subject for whom features and a responsiveness are provided to train a machine learning classifier. Responsiveness may be a binary classification, such as if a training subject is classified as having responded to a treatment if the subject exhibited a predefined response, including an extended life span, a shrinking of a tumor, partial or complete remission, etc.). In other examples, responsiveness may be a score or value based on a degree of responsiveness obtained rather than a binary assessment of whether responsiveness was or was not obtained. For example, a machine learning classifier according to the present disclosure may include classification and regression trees depending on the type of prediction sought, as non-limiting examples.

A machine learning classifier may be any classifier that is suitable for computer-based machine learning. A non-limiting example includes a random forest machine learning classifier. In a random forest machine learning classifier, decision trees based on training subjects features and responsiveness to treatment value are created, with nodes representing classification decision points and leaves representing outcomes based on trained inputs. A random forest classifier may produce multiple trees using subsets of features and subsets of training subjects to create numerous trees that are then aggregated. Such multiple decision trees containing subsets of inputs prevent overfitting and reduces error and bias in a prediction. In some examples, the more decision trees created during training the more accurate a machine learning classifier may result. In some examples, anywhere from 5,000 to 500,000 decision trees may be created during training. For example, 5,000, 10,000, 15,000, 20,000, 25,000, 30,000, 50,000, 75,000, 90,000, 100,000, 125,000, 150,000, 175,000, 200,000, 225,000, 250,000, 275,000, 300,000, 325,000, 350,000, 375,000, 400,000, 425,000, 450,000, 475,000, or 500,000 decision trees may be run and aggregated in a random forest machine learning classifier. More or fewer trees may be run instead, as may numbers in between these exemplary possibilities.

Numerous options are available for performing random forest training and generating a prediction from a random forest classifier. As a non-limiting example, R programming language may be used. Other classifiers may also be used in accordance with aspects of the present disclosure as well, including, without limitation, a neural network classifier, a support vector machine, a max entropy classifier, an extreme gradient boosting classifier, and a random fern classifier.

According to a method disclosed herein, features are obtained from each of a number of training subjects, as are a responsiveness of each such subject. Such features and responsivenesses, or inputs, are entered into a computer memory store, such as a hard drive, server, or other memory component. Also stored on a memory storage feature of such computer are instructions, contained in software, that instruct a one or more microprocessors. The instructions include instructions for using the input from the training subjects to create a machine learning classifier. A trained machine learning classifier is then stored in one or more computer memories and may subsequently be run on features from a subject for whom a prediction as to responsiveness is sought.

As a non-limiting example, instructions may instruct one or more microprocessors to perform random forest training, creating decision trees from the training subject input for ascertaining whether the presence, absence, level, etc., of various features are more or less likely to indicate responsiveness to a treatment, and to aggregate the numerous decision trees into a trained random forest machine learning classifier. A trained machine learning classifier according to this example, based on the aggregation of decision trees produced by the one or more microprocessors when processing the features and responsivenesses in accordance with the instructions, may then be stored in one or more memories. Subsequently, when a prediction as to whether a non-training subject (i.e., a subject whose feature values were not used to train the trained machine learning classifier) will be responsive to a treatment such as with a particular checkpoint inhibitor, features obtained from a tumor sample of said non-training subject may be loaded into one or more memories. One or more microprocessors may process instructions such that the non-training subject's features are analyzed by the trained machine learning classifier, accessed from one or more memories by one or more microprocessors, and a prediction as to the subject's responsiveness reported.

In such an example, the machine learning classifier was the trained machine learning classifier was trained on features of tumor samples obtained from each of a plurality of training subjects and a responsiveness of each of the plurality of training subjects to a treatment comprising a checkpoint inhibition, wherein the machine-learning classifier was trained to predict responsiveness to the treatment. Furthermore, genomic information of a non-training subject including non-training features from a subject tumor profile, or set of feature values, were input to the trained machine learning classifier to generate a treatment responsiveness classification for the non-training subject, such as a classification or score indicating a prediction of how the non-training subject would respond to the treatment. The treatment may be a checkpoint inhibition.

A checkpoint inhibition responsiveness for a non-training subject generated by the trained machine learning classifier may be reported to a user. A report may include a classification of the subject indicating, in a binary manner, whether or not the non-trained subject is predicted to respond to the treatment. In other examples, a numerical score on a scale may indicate probability of responsiveness in addition to or rather than a binary classification of whether or not the non-training subject is predicted to respond. In other examples, specific degrees of responsiveness may be reported. For example, a report may indicate a high likelihood of responsiveness, but responsiveness may be qualified as to duration or degree. In other examples, a report may indicate a prediction of a relatively lower likelihood of responsiveness but of a greater duration or degree if such non-training subject is predicted to respond.

A report of a prediction, as a score or a binary prediction of likely to respond as opposed to unlikely to respond, may be reported by a graphical user interface (GUI). For example, a computer or computer system connected to a one or more memory and one or more microprocessors wherein a non-training subject's profile of feature values were entered and analyzed by a trained machine learning classifier may further be connected to a display device on which a prediction is reported visually. A GUI may take any of many forms. For example, a GUI may be a tabulation of various aspects of features or a subset of features with a higher degree of importance or weight in generating the prediction, as well as whether each such factor indicated a higher or lesser likelihood of the non-training subject responding to a treatment (i.e., the feature's valence) in view of the feature's value for the non-training subject, as further explained below. Or, a report may include different shapes, shading, or color schemes for reporting such information.

A report of a prediction classification using a constellation of features as disclosed herein differentiates the subject matter disclosed herein from conventional methods for predicting responsiveness to treatment. Unlike conventional treatment prediction methods, herein is disclosed a method employing a combinatorial approach where, in some examples, a high number of features may be queried in context with each other rather than one or merely a few in isolation in generating a prediction. Such a distinction of the herein disclosure over conventional methods is advantageous in that efforts heretofore to predict whether an individual will respond to a given treatment such as a checkpoint inhibitor have to date been of very limited accuracy and generalizability, based on limited numbers of features. As disclosed herein, an unconventional machine learning process for assessing contributions of numerous factors and how each may independently and in concert with others affect a prediction overcomes such limitations of conventional prediction attempts.

Conventional methods for ascertaining a responsiveness prediction have related to identifying a feature or limited number of features that may indicate a higher or lower likelihood of responsiveness to a treatment. Here, by contrast, disclosed is an unconventional approach wherein a machine learning classifier is used to assess relative contributions of potentially dozens of features or more simultaneously in context with each other to formulate a prediction. Such a multifactorial approach, via an unconventional application of a machine learning classifier, provides significant benefits over currently available methods.

An advantageous feature of some GUI examples for reporting a responsiveness prediction may be in the representation of multifaceted information pertaining to features relevant to the reported prediction in a relatively tight or small space such that a user may ascertain significant information in a compact manner. In particular, an advantage of certain examples of GUIs used in accordance with the present disclosure may be their sizing and configuration on a display of limited or reduced size, or on a display upon which significant other quantities of information also need or are desired to be displayed. A GUI for reporting a prediction classification in accordance with the present disclosure may serve to pack a high amount of easily recognizable and cognizable facets of a prediction classification and/or features relevant to the generation thereof into a limited display size or limited proportion of a display. Such compact reporting improves user interfacing with a computer system giving the report in that it expedites the receipt and interpretation of a report and conserves display space that may be required for other purposes or of limited availability such as where a display is a screen of a portable electronic device such as a phone or other wireless communication device (e.g., computer tablet or phone or other portable wired or wireless device). In an example where a report is presented by a GUI that condenses a high amount of characteristics and aspects of features into a constricted space yet retains the ability to quickly convey high amounts of information that remains quickly and easily ascertainable, usability of a computer system is improved in that more display space remains available for additional purposes at the same time, or use on smaller displays remains possible.

A report may include feature identifiers, or aspects or characteristics of some or all features used in generating the responsiveness classification. For example, a report may include an indication of a feature's valence, i.e. whether its value in a user's profile indicated an increased or decreased likelihood that the subject would respond to the treatment. That is, for a non-training subject's profile, a feature may have a positive valence or a negative valence. A positive valence may mean either the feature's value in training subjects tended to be positively correlated with responsiveness to treatment and the non-training subject's value for that feature was high, or that the feature's value in training subjects tended to be negatively correlated with responsiveness to treatment and the non-training subject's value for that feature was low.

Another identifier may be an indication of a feature's importance in generating a prediction for a given machine learning classifier. Importance or a feature may indicate that it is more likely to drive a prediction in one direction or another relative to other features used in training. For example, in some examples, a Gini decrease index may be ascertained for one or more features during training. A Gini decrease index indicates importance of a feature in that it accounts for a feature's effect on a classifier's functioning relative to how much influence other features have in driving a generated prediction. A Gini decrease index may be determined with use of various software packages, such as by using R programming language. In some examples, importance's of features may be used to determine which features' identifiers are included in a report separate from or in addition to a prediction score. For example, for a given report reported in the form of a GUI, the GUI may display features of only such features whose importance meets or exceeds a predetermined minimum importance threshold. For example, a report might include identifiers of only such features whose importance, represented numerically as Gini decrease index, squared exceeds 0.1. More or less stringent minimum importance thresholds may be set instead, or altered for given reports depending on how much information is desired to be included along with a prediction score. The higher the minimum importance threshold, the fewer features' identifiers may be included in a report, and vice versa. For example, a minimum importance threshold may be where the square of the numerical importance (e.g., Gini decrease index) is above anywhere between 0.01 and 0.5. Other minimum importance thresholds may be chosen anywhere between or outside of tis range.

Another example of a feature identifier that may be included in a report is a feature's weight. A feature's weight is a measure of the degree to which that feature's value for a subject on its own would suggest the subject would or would not respond to the treatment. For example, for each feature, a single factor decision boundary may be determined. A single factor decision boundary is a value for that feature which best distinguishes between training subjects do and do not respond to the treatment. For example, if all training subjects who responded to treatment had a value for a feature above a given amount whereas all non-responding treatment subjects had values below that amount, that amount could be the single factor decision boundary. In some other examples, some responding training subjects may have a feature value above some non-responding training subjects and other responding training subject may have a feature value below those training subjects. Thus, in some examples, there may be a bright line for a feature's value that unequivocally distinguished between responders and non-responders, whereas for others there may be more overlap at the boundary of feature values between responders and non-responders. For examples of the latter type, a single factor decision boundary may be chosen as a value which provides the maximum possible distinction between responders and non-responders in the set of training subjects.

Weight of a feature is a measure or indication of how far a feature value for a non-training subject differs from the single feature decision boundary for that feature. The more a value for a feature for a non-training subject differs from the single factor decision boundary for that feature based on the training subjects, the greater the weight that feature may have in determining a responsiveness classification prediction. For example, a feature may have a negative valence, meaning a non-training subject has a low value for a feature positively correlated with responsiveness in training subjects, or a high value for a feature negatively correlated with responsiveness in training subjects. If a non-training subject's value for that feature differs substantially from the single factor decision boundary for that feature, the weight of that feature may be high. However, if another feature has a higher importance, and a positive valence (i.e., high value for the non-training subject and positive correlation with responsiveness in training subjects, or low value in non-training subject and negative correlation with responsiveness in training subjects), it may have a proportionally stronger influence on the responsiveness prediction classification even if its value differs less from the single factor decision boundary (i.e., has less weight).

Numerous possibilities are available for presenting feature identifiers as a component of a responsiveness prediction report and GUI. Several specific examples are presented herein in some detail. However, a skilled person would appreciate that there may be many other possibilities for reporting valence and weight and importance of features in a GUI report and that the examples given here are not limiting or each on its own in any way essential specifically.

A GUI may present tabulated features with rows and columns. Features may be presented in, for example, rows, and different characteristics of given features may be presented in multiple columns. For example, different columns may indicate the importance of a feature, its valence, the single factor decision boundary for that feature, a non-training subject's value for that feature, optionally with a visual indication of how much the non-training subject's value for that feature differs from the single factor decision boundary for that feature, and whether the non-training subject would be predicted to respond if the prediction were based on that feature alone. A tabular GUI may include any combination two or more of the foregoing. A tabular GUI report may also include an overall prediction score.

A GUI may also be a histogram. For example, columns may indicate a value for a given feature for a non-training subject, with a line also indicating the single factor decision boundary for that feature. A difference between the value for the feature for the non-training subject and the line indicating the single factor decision boundary is an identifier of weight for that feature. A line may also be drawn between the height of the column and the line indicating the single factor decision boundary. The length of the line between the two also is an indicator of weight. Valence may be indicated by a symbol below the column. For example, a plus or minus sign may indicate a positive of negative valence, respectively. Other pairings could include upwardly and downwardly pointing arrows, upwardly and downwardly oriented triangles, etc., where one direction indicates a positive valence for that feature and the other orientation indicates a negative valence. Valence may also be indicated by color or shading of the column, with columns of one color or shading pattern indicating one valence (positive or negative) and columns of a different color or shading pattern indicating the opposite valence. Color or shading of a line between a value for a non-training subject's feature in the histogram and the single factor decision boundary for that feature may also indicate valence. For example, if a feature's value is negatively correlated with responsiveness in training subjects and the non-training subject's value for the feature is less that the single feature decision boundary, a line connecting the non-training subject's value in the bar of the histogram report for that feature and the single factor decision boundary may be a color or shading indicating positive valence. Whereas, if a feature's value is positively correlated with responsiveness in training subjects and the non-training subject's value for the feature is less that the single feature decision boundary, a line connecting the non-training subject's value in the bar of the histogram report for that feature and the single factor decision boundary may be a color or shading indicating negative valence. Note that in both instances the non-training subject's value for the feature is less than the single factor decision boundary for that feature but its valence differs, depending on whether the feature was negatively (positive valence) or positively (negative valence) correlated with responsiveness in training subjects. The converse would also be true (i.e., where a feature's single feature decision boundary is less than a non-training subject's value for that feature, it may have positive or negative valence depending on whether the feature tended to be positively or negatively correlated with responsiveness in the training subjects, respectively).

Importance of a feature may be indicated by a symbol or other indicator near, within, or below the column for that feature in the histogram. For example, size of a symbol below the bar for a feature may indicate its importance. Or importance may be color coded, with bars or associated symbols colored or shaded in such a way as to indicate the degree of importance. A key may accompany the histogram indicating a spectrum of colors or shades with higher importance indicated by a color or shade more similar to one end of the spectrum and lower importance indicated by a color or shading pattern more similar to the other end of the spectrum. In some examples, a symbol, such as placed below a bar in a histogram GUI report for a non-training subject's feature, may indicate whether values for the feature were negatively or positively correlated with responsiveness in training subjects. For example, a plus sign and minus sign, upwards arrow and downwards arrow, upwardly-pointing triangle and downwardly pointing triangle, or other pairings, may signify positively and negatively correlated features. In such cases, relative sizes of such symbols may signify relative importance thereof.

In another example, a GUI report includes shapes that convey identifiers for features. For example, each feature whose identifiers are included in a GUI report may be represented by a shape whose dimensions, color, shading, or other aspects may designate different identifiers. For example, features may each be represented by rectangles, with width representing importance and height weight. A color or shading or outline pattern of the rectangles may indicate valence. Or the features may be represented by triangles, with the base representing importance and the height weight, or vice versa. A triangle may point up for a feature with positive valence and vice versa. Or a color of the triangle or shading pattern or pattern of lines in which its outline is drawn may indicate valence.

In another example, identifiers of a feature may be indicated in the shape of sector of an annulus, or annulus sector. The angle of the annulus sector may indicate importance and its outer radius its weight, or vice versa. Valence may be indicated by a color of the annulus sector, or pattern in which it is shaded, or patterning of a line in which its outline is drawn. In other examples, a sector of a circle, or circle sector, may represent identifiers of a feature, with angle and radius representing importance and weight or vice versa, and color or shading, etc., representing valence as for the example of an annulus sector given above. Where feature identifiers are represented by annulus sectors, in some examples all such annulus sectors may be drawn to have the same inner radius, and the annulus sectors may be arranged such that their inner arcs together form an inner circle. Within the inner circle itself a prediction score or other overall summary or indication of responsiveness prediction or classification may be indicated. Color or shading of said inner circle may indicate whether the responsiveness classification prediction predicts a non-training subject is likely to respond or not likely to respond. For example, where the prediction is that the non-training subject is likely to respond, the inner circle may have one color or shading pattern or be drawn in a line of one pattern, whereas if the prediction is that the non-training subject is not likely to respond the inner circle may have a different color or shading pattern. In other examples, rather than an inner circle there may be another inner shape such as a square or star or triangle or pentagon or other shape. Size of the inner shape may indicate the strength of the prediction, with a larger inner shape signifying higher confidence in the prediction and vice versa.

A GUI report may also provide a user with the opportunity to seek more information or launch additional software applications depending on interest in particular features as reported in the GUI. For example, the GUI could be configured such that a user could hover a pointer or other element controllable by an input device such as a mouse over identifiers for a feature, or by touching a touch screen. Orienting the element or touching the display at a feature could open a drop-down menu with options that could be further selected. For example, a drop-down menu could display aspects of the feature specific to the non-training subject such as its value, or a cohort range for the feature, what percentage the non-training subject's value for the feature represented relative to the range of values present in the training data, or compared to only training data for training subjects who responded in the way the non-training subject was predicted to respond, or for the other training subjects, or the features single factor decision boundary, or a feature's importance or correlation with responsiveness for other treatments, or any combination of two or more of the foregoing. A drop-down menu may also present links to other programs accessible by one or more microprocessors for further evaluating a feature or a non-training subjects prediction score, such as running a different machine learning classifier. By compacting such interactivity into a GUI report, significant space and computational resources could be conserved and user interactivity with the computer system significantly enhanced. For example, less display space would be needed for simultaneous continual display of the GUI report during access of drop down menu options. Furthermore, time and computing resources would be conserved as such interactivity would permit accessing multiple computer functions without switching between display screens or applications.

In some examples, a trained machine learning classifier may be further trained. For example, one a non-trained subject's responsiveness to a treatment is ascertained, the machine learning classifier may be retrained on features including the training subjects feature values and responsivenesses on which it was initially trained plus the feature values and responsiveness for the non-training subject for which a prediction was provided and responsiveness obtained. In other examples, a trained machine learning classifier may be retrained with additional feature values and responsiveness of a non-training subject for whom a prediction was not obtained from the trained machine learning classifier.

In some examples, upon obtaining a response prediction classification for a subject, a decision of whether or not to apply a given checkpoint inhibition treatment may be made. A high prediction score as to a particular checkpoint treatment obtained from a machine learning classifier trained as disclosed herein may be followed by a decision to treat the subject with the treatment for which the machine learning classifier was trained to predict responsiveness. Or, a low score may be followed by a decision not to apply such treatment. Someone obtaining a response prediction classification or a score indicating a suitably high likelihood of responsiveness, or instructions to treat a subject as a result of such a response prediction classification or a score having been obtained, in accordance with methods, systems, or a machine learning classifier as disclosed herein, may treat the subject with the treatment. Included in the present disclosure is treating cancer in a subject by administering a checkpoint inhibition treatment in response to obtaining a response prediction classification or a prediction score, generated in accordance with the present disclosure, indicating that the subject would respond to such treatment, or administering such treatment on the instructions of someone who obtained such a response prediction classification or a prediction score.

EXAMPLES

The following examples are intended to illustrate particular embodiments of the present disclosure, but are by no means intended to limit the scope thereof.

FIG. 1 is a web diagram showing options for performing a method in accordance with aspects of the present disclosure. Shown are potential, non-limiting examples of sources of feature values, such as the cancer genome atlas (TCGA), or data from clinical trials (such as trials for treatment with anti-PD1 treatment, anti-CTLA4 treatment or other checkpoint inhibitor treatment or other cancer treatment). Some non-limiting examples of assays that may be used for obtaining feature information used to determine feature values are also indicted, such as RNAseq and whole exome sequencing (WES), as two non-limiting examples. Different non-limiting examples of types of features are also indicated, as are examples of which assay or assays may provide measures relevant to ascertaining a value for such feature. Examples include HLA, gene expression, ssGSEA, tumor mutational burden, cytolytic infiltration such as by tumor infiltrating lymphocytes (deconvoluted), CGA, neoantigens, presence of clonal and/or subclonal mutations (i.e., mutations that are present in descendants of a cell that initially presented a given mutation, and others of a cell descendant from such initially mutated cell that subsequently acquired another mutation), etc. Features are the processed by a machine learning (ML) model whereby a machine learning classifier is trained and a non-training subject's feature values are input to the trained machine learning classifier, whereupon a patient response is obtained for labeling the non-training patent as likely or unlikely to respond to the treatment.

FIG. 2 shows some non-limiting examples of features that may be relevant in training a classifier and predicting a patient's responsiveness to treatment in accordance with aspects of the present disclosure. As would be understood by skilled artisans, the features identified in FIG. 2 are non-limiting examples. They are also not all required. Others than those shown in FIG. 2 may be employed whereas some shown may be omitted in performing a method in accordance with aspects of the present disclosure. Features here are shown as grouped according to function, cellular or molecular pathway or response, etc. Examples of such groupings include antigen presentation, T cell or NK cell signatures, signatures of immunologically mediated cytolysis, checkpoint pathway participants, interferon γ pathway participants, and MDSC/Treg signatures. Other groupings representing other functions or cellular or molecular processes, etc., may be included in addition to or instead of any of those shown here as non-limiting examples.

Figure 3:
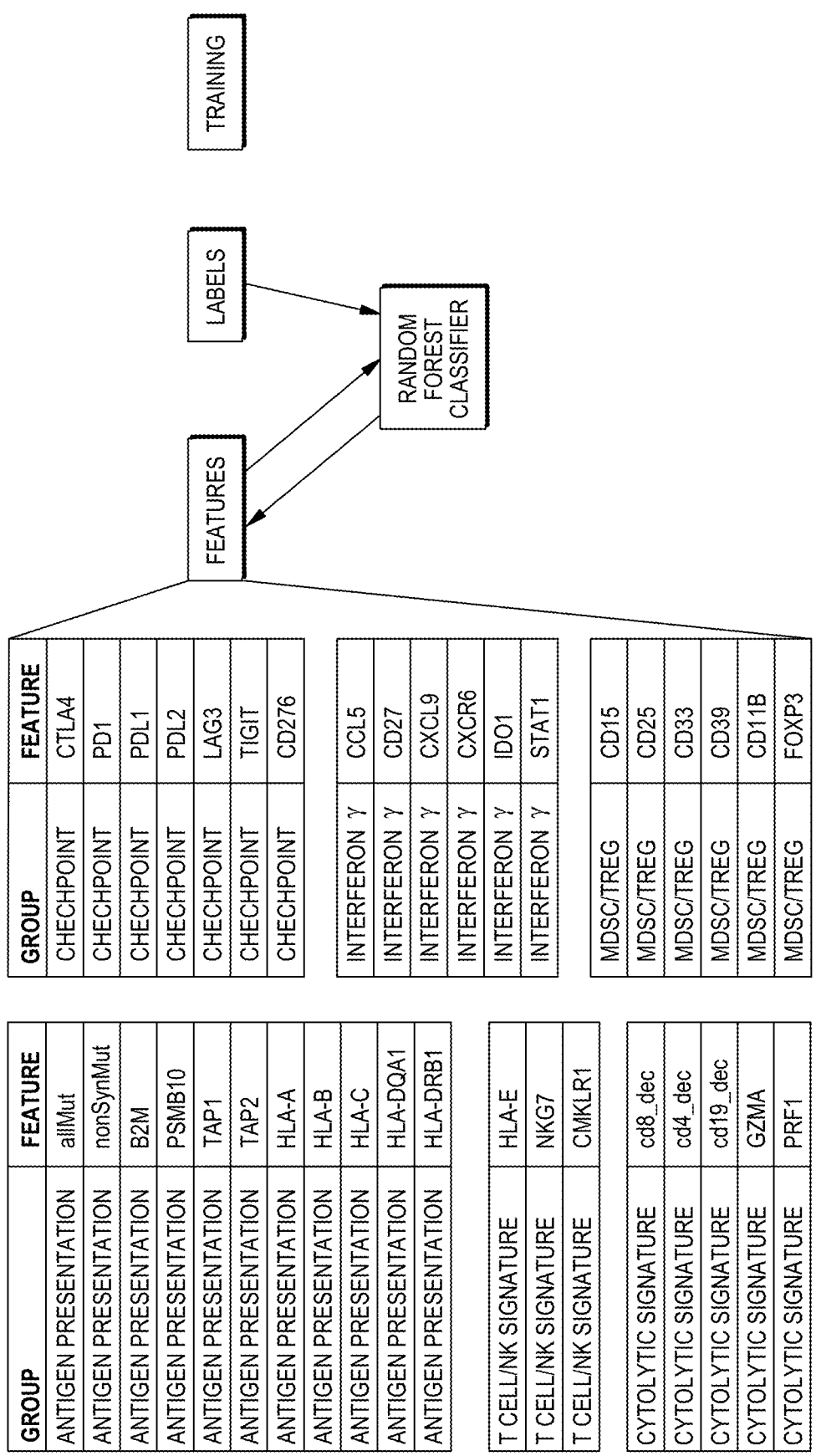
FIG. 3 is a web diagram showing an example of how a method of training a classifier may be performed in accordance with aspects of the present disclosure.

FIG. 3 is a web diagram showing an example of how a method of training a classifier may be performed in accordance with aspects of the present disclosure. As would be understood by skilled artisans, the features identified in FIG. 3 are non-limiting examples. They are also not all required. Others than those shown in FIG. 3 may be employed whereas some shown may be omitted in performing a method in accordance with aspects of the present disclosure. Features here are shown as grouped according to function, cellular or molecular pathway or response, etc. Examples of such groupings include antigen presentation, T cell or NK cell signatures, signatures of immunologically mediated cytolysis, checkpoint pathway participants, interferon γ pathway participants, and MDSC/Treg signatures. For training, as indicated by FIG. 3, features from training subjects, such as those shown, are inputted to a machine learning classifier such as a random forest classifier as are labels corresponding to how the trained subjects responded to a given treatment such as a checkpoint inhibition treatment. In this manner, the classifier is trained. As disclosed, other machine learning classifiers may also be used.

Figure 4:
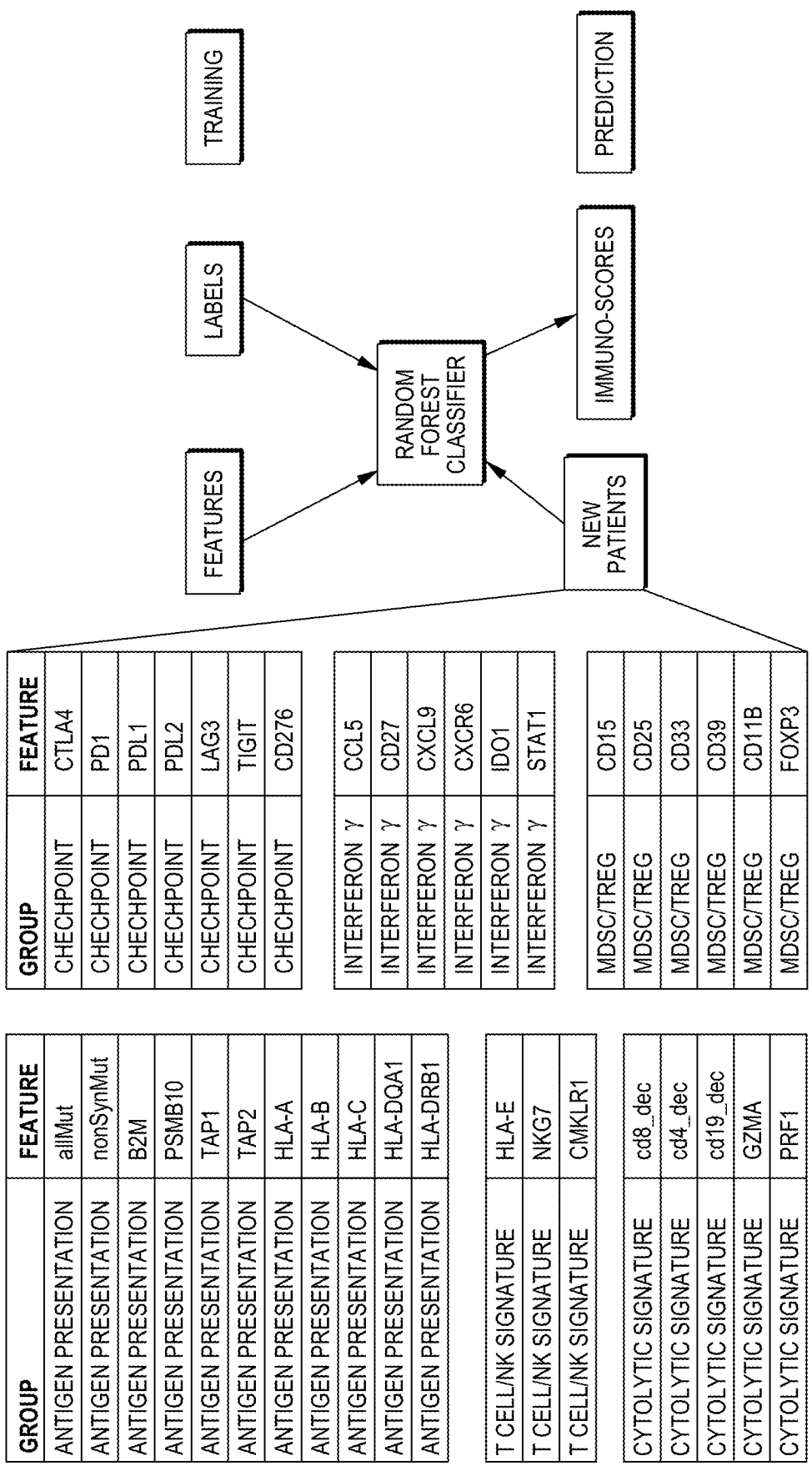
FIG. 4 is a web diagram showing an example of how a method of using a trained classifier to predict a subject's responsiveness to treatment may be performed in accordance with aspects of the present disclosure.

FIG. 4 is an expansion of FIG. 3, showing a web diagram showing an example of how a method of using a trained classifier to predict a subject's responsiveness to treatment may be performed in accordance with aspects of the present disclosure. A machine learning classifier (in this non-limiting example, a random forest classifier) having been trained on features (non-limiting examples of which are shown here for example), receives further input obtained from a non-training subject. In particular, feature values from the non-training subject are input to the machine learning classifier. The trained machine learning classifier then generates a response prediction classification which may include a score indicating likelihood of responsiveness (here indicated as immuno-scores) and/or identifiers of features, in reporting a prediction.

Features and responsiveness to PD-1 inhibition were obtained from Hugo et al. (2016) Genomic and Transcriptomic Features of Response to Anti-PD-1 Therapy in Metastatic Melanoma. Cell. 2016; 165(1):35-44. In that study, whole exome sequencing data and RNAseq data were obtained from tumor samples from 26 patients with melanoma were obtained pre- and -post treatment with an inhibitor of PD-1 checkpoint pathway (anti-PD-1 antibody treatment (nivolumab) or anti-PD-L1 antibody treatment (pembrolizumab). Raw data were publicly available and accessed for the examples herein. Transcriptome data obtained via RNAseq (including expression levels of transcripts in the samples) was available online from the National Center for Biotechnology Information (NCBI) Gene Expression Omnibus at accession number GSE78220. Whole-exome sequencing data obtained by NGS methods was available online from the NCBI Sequence Read Archive under accession numbers SRA: SRP067938 and SRA: SRP090294. Responsiveness of the patients for whom such data were available were also obtained from the results of the published studies. Data were selected from these sources to create features for training subjects and responsivenesses for training subjects to train a machine learning classifier to predict responsiveness to anti-PD1 checkpoint pathway inhibitors. Data for features for obtaining a prediction from a trained machine learning classifier were also obtained from these sources.

Features and responsiveness to CTLA-4 inhibition were obtained from Van Allen et al. (2015) Genomic correlates of response to CTLA-4 blockade in metastatic melanoma. Science 350:207-211. In that study, whole exome sequencing data and RNAseq data were obtained from tumor samples from 30 patients with melanoma were obtained pre- and -post treatment with an inhibitor of CTLA-4 (ipilimumab). Raw data were publicly available and accessed for the examples herein. Whole exome sequencing data and transcriptome data obtained via NGS methods were available online from the NCBI database of Genotypes and Phenotypes (dbGaP), accession number phs000452.v2.p1. Responsiveness of the patients for whom such data were available were also obtained from the results of the published studies. Data were selected from these sources to create features for training subjects and responsivenesses for training subjects to train a machine learning classifier to predict responsiveness to anti-CTLA4 checkpoint pathway inhibitors. Data for features for obtaining a prediction from a trained machine learning classifier were also obtained from these sources.

From data obtained from both studies, data was pre-processed to create features input to machine learning classifiers for training. Random forest machine learning classifiers having received such input were then trained on training data. Features from some subjects was then used to generate a prediction from one or both trained classifiers and a responsiveness prediction classification was reported via a GUI, including a prediction score and identifiers of features. FIG. 1 as described above presents an overview of an example of some methods used in these examples. FIG. 2 shows 38 features that were selected for inputting to a machine learning classifier. Features were selected based on expectations that they may relate to a prediction of whether a subject may or may not respond to checkpoint inhibition based on current understanding of the roles of such features. allMut refers to tumor mutational burden all mutations and nonSynMut refers to tumor mutational burden attributable to nonsynonymous mutations. cd8_dec, cd4_dec, and cd19_dec refer to tumor infiltrating lymphocyte deconvolution measures for the respects CD8, CD4, and CD19. The remaining features identified in FIG. 2 were obtained from RNAseq data and include measures of relative expression levels. For some examples, ssGSEA was also obtained for sets of features (antigen presentation, T cell/NK cell signature, immunological cytolytic signature, checkpoint pathway, interferon γ, and MDSC/Treg signatures). Some machine learning classifiers were trained on only the original 38 features and others were trained on the 38 original features plus the gene sets obtained by ssGSEA analysis resulting in a total of 44 features for such examples.

Subjects' data per feature value were normalized by rank ordering their values as a percentage each value per feature relative to the range of values for all subject's values for that feature in the set. Responsiveness for the training in these examples was binary, with a subject labeled as either being responsive (including both partial responsivenesses and full responsiveness or long-term benefit from treatment as reported in the respective underlying study) or not responsive (including subjects reported as having disease progression in response to treatment and no benefit of treatment reported in the underlying studies).

Features were inputted to a computer system including one or more memory stores and one or more microprocessors. The one or more memory stores contained instructions which, when run by the one or more microprocessors, trained a random forest machine learning classifier using R programming language. Subjects features were stores on the one or more memory stores and analyzed by the one or more microprocessors according to the instructions. In these examples, 50,000 trees were used. After training, a subject's features were the input to the trained machine learning classifier, as stored on the one or more memory stores of the computer system, and a response prediction classification score generated and reported by a GUI on a computer display. An example of training is shown in FIG. 3 and an example of generating a prediction is shown in FIG. 4.

Final prediction scores were generated by the probability of classification, scaled to a 0-10 score. As an example, by way of explanation, a 0.75 probability of classified in "has response" to a given immunotherapy was translated to a responsiveness prediction score of 7.5. Furthermore, for each feature, a single factor decision boundary was determined at the value that maximize the classification accuracy. The correlation direction of whether a feature was positively or negatively correlated with classification as responsive was determined by the spearman correlation between the feature and response. The foregoing analyses were carried out using full samples without separation of training and non-training subjects. Performance analysis were carried out separately. For 3-fold cross-validation and area under the curve (AUC) plotting, R programming language package "caret" and "cvAUC" were used with default function and parameter.

FIG. 5 shows an example of a report of a GUI 500 reporting response classification prediction score and feature identifiers. For these examples, identifiers of a feature were presented only if a square of the feature's importance (importance being determined by the feature's Gini index decrease) was greater the 0.1. FIG. 5 shows a GUI report for a subject whose data was obtained for an anti-PD1 trial run on a machine learning classifier trained to predict responsiveness to anti-PD1 treatment (e.g., anti-PD1 or anti-PD1-L1 antibody). The 15 features with importances that exceeded the minimum importance threshold are shown in the FEATURES column 510. The features' importances are shown in the IMP. column 520. The group the feature is associated with as per FIG. 2 is shown in the column GROUP 530. A feature's positive or negative correlation with responsiveness is shown in the CORR column 540. In this example, triangles are used to indicate the direction of correlation, with an upwardly pointing triangle indicating positive correlation and a downwardly pointing triangle indicating negative correlation between a feature value and responsiveness. A feature's single feature decision boundary is shown in column 1FDB 550. In this example, the single factor decision boundary is identified numerically as the percentage within the range of subject values for that sample above and below which provided the highest obtainable distinction between responders and non-responders (i.e., a value above or below that percentage was less accurate overall in distinguishing between a responsive and a non-responsive subject). Single factor decision boundary is also indicated by shading from left to right within each feature's cell in the 1FDB column, representing the percentage indicated by the single factor decision boundary (i.e., a low percentage has less shading and a higher percentage has more shading, proportional to the value of the boundary). The subject's value for each feature is shown in the INPUT column 560 (in this case PT5 INPUT, identifying the patient for whom the prediction is here reported as patient number 5, or PT5). The number in PT5 INPUT column 560 indicates the subject's value for a given feature as well as shading indicating the percentage rank of that subject's feature value relative to the range of values for training subjects.

Whether the subject would have been predicted to respond to treatment based solely on the value of a given feature is reported in the column 1F.PRED 570. Thus, for positively correlated features, if the value in PT5 Input 560 exceeds the value in 1FDB 550, 1F.PRED 570 indicates YES (meaning that feature would predict that the subject would respond to treatment). For positively correlated features, if the value in PT5 Input 560 is below the value in 1FDB 550, 1F.PRED 570 indicates NO (meaning that feature would predict that the subject would not respond to treatment). For negatively correlated features, if the value in PT5 Input 560 exceeds the value in 1FDB 550, 1F.PRED 570 indicates NO (meaning that feature would predict that the subject would not respond to treatment). And for negatively correlated features, if the value in PT5 Input 560 is below the value in 1FDB 550, 1F.PRED 570 indicates YES (meaning that feature would predict that the subject would respond to treatment). In this example, cells in 1F.PRED 570 may also be color coded in accordance with whether the feature alone would predict responsiveness. YES cells may be colored green, for example (R), whereas NO cells may be colored red (R). The bottom row FULL MODEL 580 reports the response classification score, in this case 5.5. A cutoff may be determined above or below which a treatment may be predicted to be effective or not effective. For example, a score below 5.0 may be taken as a prediction that the treatment would not work for this patient and a score above 5.0 may be taken as an indication that the treatment would work for this patient. In this case, with a score above 5 being taken as an indication that the treatment would work for this patient, it can be seen that the value of training and using a machine learning classifier as disclosed herein provides a significantly improved basis for prediction than would basis prediction on only one of the features whose indicators are presented in the GUI report, in that some features alone predicted non-responsiveness (including the feature with the highest importance) but the machine learning classifier overall predicts that the patient would respond.

In this example, a response prediction score is reported by the GUI, as are indicators for each feature included in the GUI report, including weight (by offering a comparison between PT5 INPUT 560 and 1FDB 550), importance 520, and valence 1F.PRED. In some examples, a user could have the option of accessing drop down menus from different aspects of the GUI such as by touching a portion of a touchscreen display corresponding to a portion of the GUI report or moving a graphical element such as a cursor with a device such as a mouse over a feature or related indicators or scores thereof to access additional information or select from additional analysis that could be run via different programming instructions on the one or more microprocessors stored on the one or more memory stores.

Figure 6:
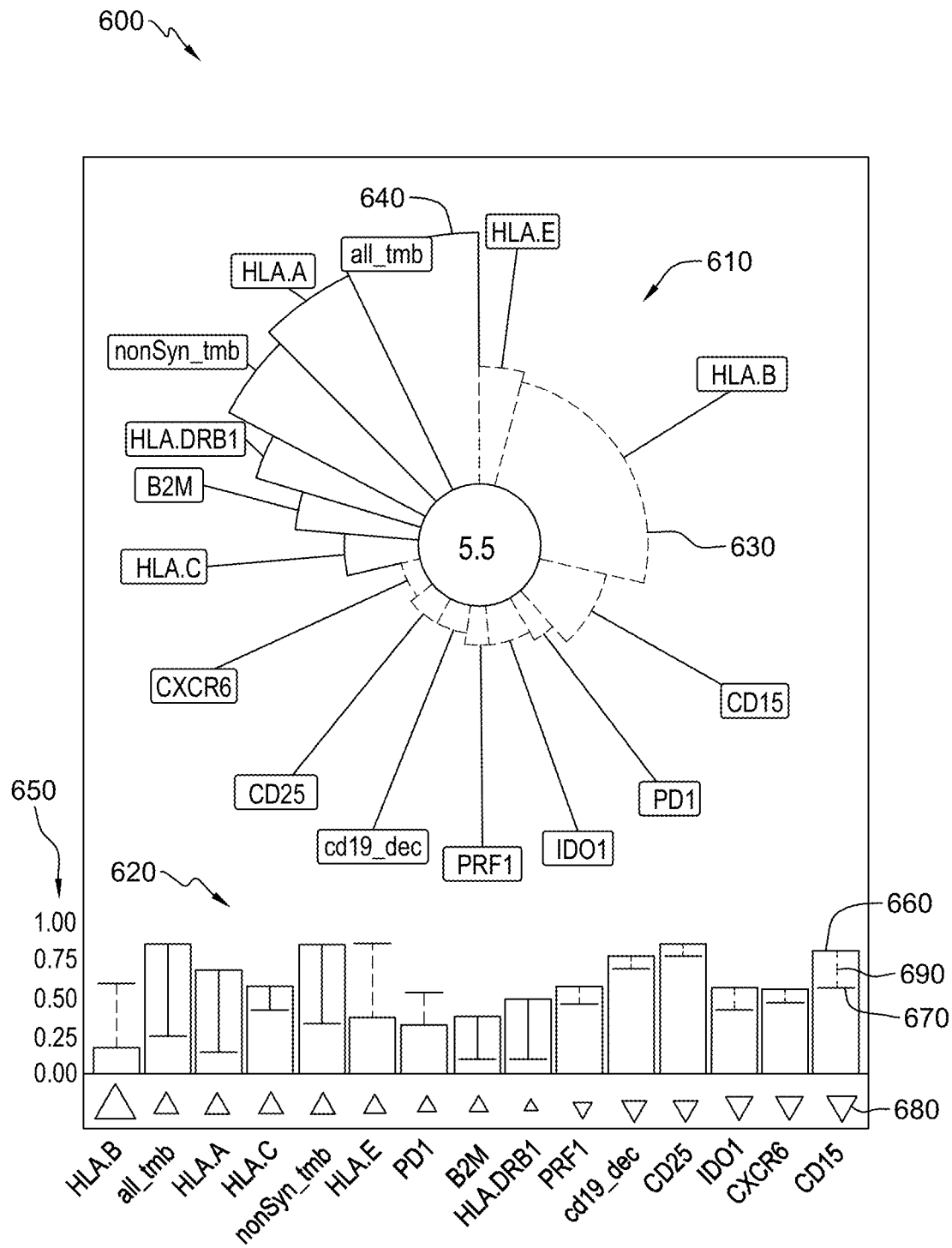
FIG. 6 is an example of a method of reporting a subject's responsiveness to a treatment as predicted by a trained machine learning-based classifier in accordance with aspects of the present disclosure.

Another GUI report 610 for this subject is presented in FIG. 6. Multiple GUI reports are combined into a single report in the example presented in FIG. 6. The upper portion of FIG. 6 presents a ring of annulus sectors 610, each corresponding to a feature whose importance exceeded the minimum importance threshold as explained for FIG. 5. The feature to which each annulus sector corresponds is also indicated in writing. For example, the annulus sector corresponding to feature HLA.B is indicated by 630. Each annulus sector has an angle, an outer radius, and an inner radius, and an inner arc. In this example, the angle corresponds to the feature's importance. In this example, the angles of the features are proportional to one another to permit direct visual comparison. Also in this example, the difference between the outer radius and the inner radius corresponds to its weight (i.e., subject's feature value's difference from the single factor decision boundary). The valence of a feature in this example is also reported by the style of line which outlines the feature's annulus sector. A feature whose annulus sector has a positive valence for a subject (such as for all tumor mutational burden 640) is outlined with a solid line while a feature whose annulus sector has a negative valence for a subject (such as for HLA.B 630) is outlined with a dotted line.

In this example, the inner arcs are arranged so as to form an inner circle. Also in this example, within the inner circle a responsiveness prediction classification score for this patient is reported, in this case 5.5. Also in this example, the overall prediction is indicated by a solid line forming the inner circle, meaning the subject's response prediction classification score exceeds the predetermined level distinguishing between a prediction of responsiveness and non-responsiveness. In other examples, a dotted line could form the or an inner circle if the response prediction classification score was below such predetermined score threshold. In other examples, color or difference shading patters within an annulus sector and/or inner circle, and/or differential coloring of outlines of an annulus sector or inner circle, may indicate valence.

Figure 10:
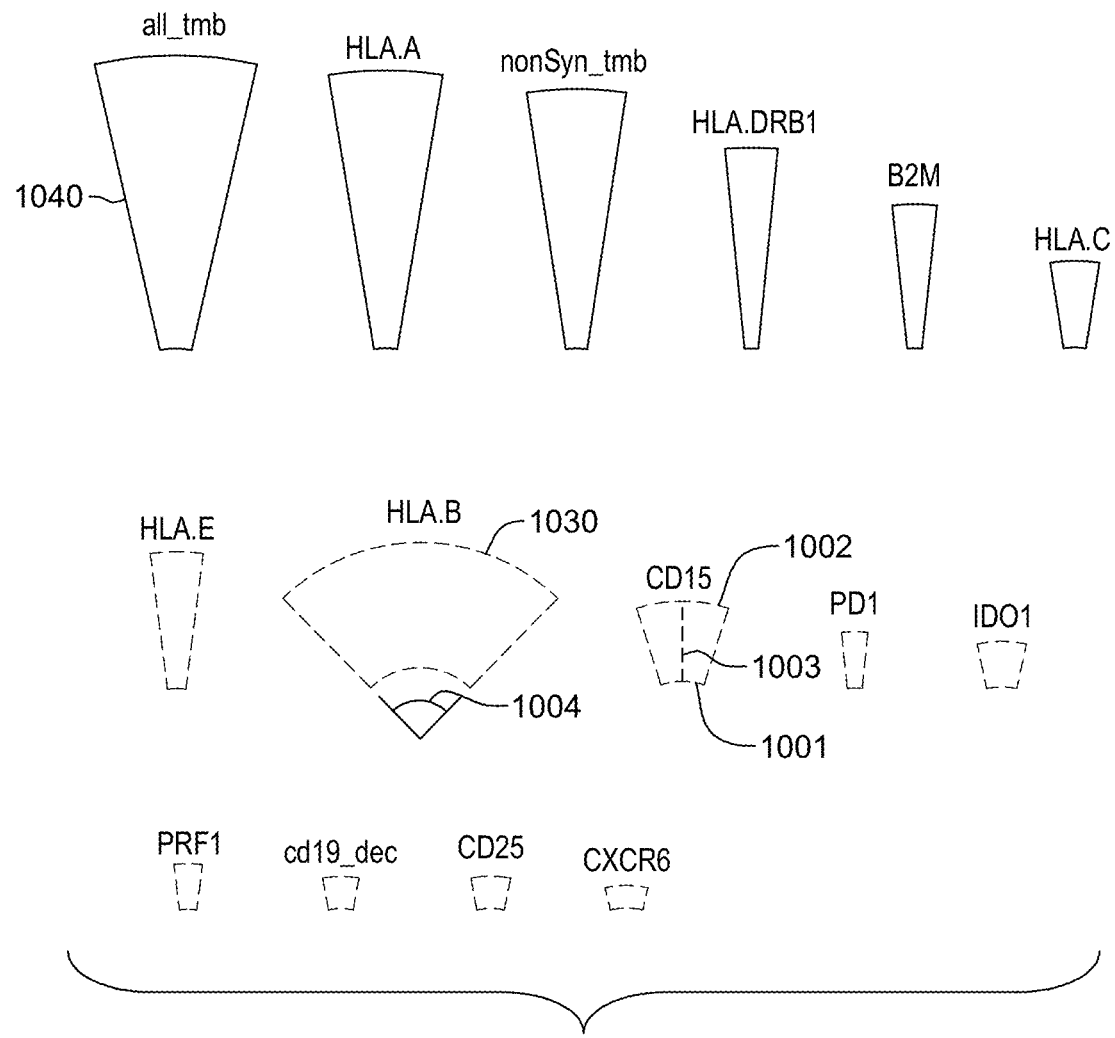
FIG. 10 is an example of a method of reporting a subject's responsiveness to a treatment as predicted by a trained machine learning-based classifier in accordance with aspects of the present disclosure.

In this example, the upper portion 610 of the GUI report presented in FIG. 6 600 includes a report of a response prediction classification score and features' importances, valences, and weights are indicated. Another example of such a GUI report 1010 is presented in FIG. 10. Annulus sectors for features are presented individually rather than with their inner arcs forming a circle. Examples of an outer arc 1002, inner arc 1001, and difference between an outer and inner radius 1003 are shown for the annulus sector for CD15 and an angle for an annular sector 1004 is shown below the annulus sector for HLA.B 1030 for illustrative purposes. Features' outer radii (or difference between inner radii and outer radii) report weight, angles report importance, and pattern of line outlining an annulus sector report whether a feature has a positive (solid line, e.g. the annulus sector for all tumor mutational burden, all_tmb 1040) or negative (dotted line, e.g. the annulus sector for CD15) valence. Not shown but also optionally included in such a GUI report 1010 is a response prediction classification score. Rather than different patterned outlines, different colors or patterned shading could be used to indicate a feature's valence. Shapes other than annulus sectors could also be used. For example, features could be reported as rectangles, with importance and weight represented by width and height, for example, or triangles with base width reflecting importance, height representing weight, and orientation representing valence. A skilled person would appreciate that numerous possibilities could be adapted for purposes of reporting multiple indicators of multiple features of a report GUI in accordance with aspects of the present disclosure.

Returning to the GUI report 600 depicted in FIG. 6, below the upper portion of the report that includes annulus sectors 610 is a histogram portion of a GUI report 620. A GUI report can have both such portions or only one, or neither. The histogram 620 shows a column for each feature whose value for the reported on subject exceeds the minimum importance threshold set for that feature. The scale on the left 650 indicates the percentage rank of the subject's value for each feature. Each feature's column represents the subject's feature value for that feature as a percentage of the range of values for the training subjects values. An example is indicated for the subject value for feature CD15 660. Also presented for each column as the single feature decision boundary for that feature, as a horizontal line in this case. An example is indicated for the single feature decision boundary for feature CD15 670. Triangles below each column indicate whether the feature is positively (upwardly pointing triangle) or negatively (downwardly pointing triangle) correlated with responsiveness. An example is indicated for CD15 680. Triangles are also proportioned to reflect relative importance of each feature, with larger triangles representing higher importance and smaller triangles representing lower importance. A line between a subject's feature value and the single factor decision boundary for that feature indicates weight of that feature. An example of a report of weight for a feature is indicated for feature CD15 690. Valence for a feature is indicated by whether the weight line is solid (positive valence) or dotted (negative valence). As would be appreciated by a skilled person, each of these particular examples for reporting different indications of different features could be omitted, or substituted with different graphical representations. Colors and shading could represent valence and/or correlations for features, arrows or other directional shapes could represent valence or correlations, importances could be represented by a scaled color coding scheme, etc.

Figure 9:
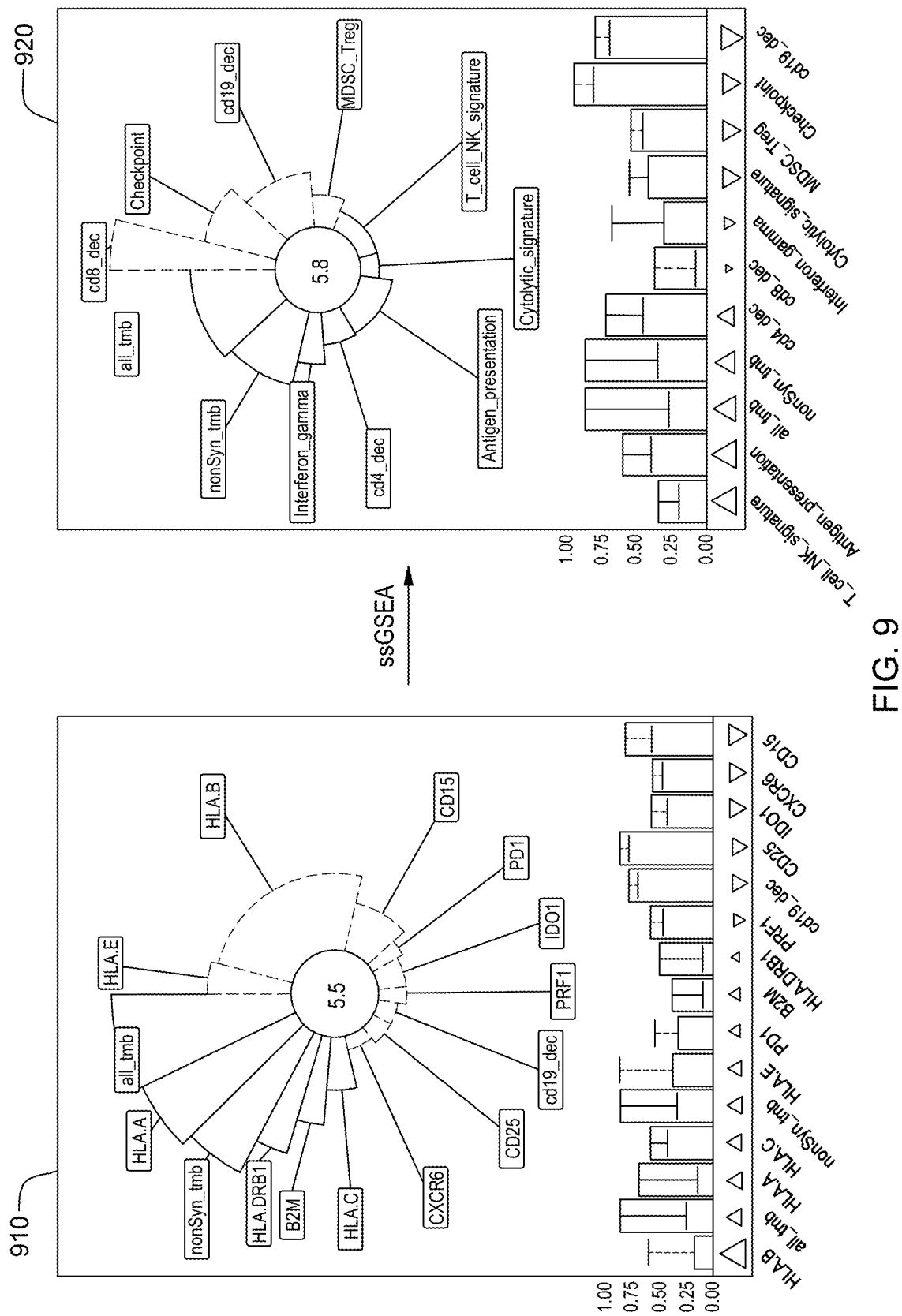
FIG. 9 is an example of a method of reporting and comparing a subject's responsiveness treatments as predicted by a trained machine learning-based classifier in when gene sets are not or are included as features in accordance with aspects of the present disclosure.

In some examples, gene sets were used to train a machine learning classifier and generate a prediction from a trained machine learning classifier. An example of gene sets, generated by ssGSEA, are shown in FIG. 7. Six sets are shown, grouped with individual features used to determine the gene set. Examples include antigen processing pathway, i.e. related to antigen presentation (710), T cell and NK cell signatures 720, cytolytic signatures 730, checkpoint pathway 740, interferon gamma 750, and MSDC/Treg signatures 760. Correlations and importances for each feature, including cell sets, when used to train a PD1 and a CTLA4 machine learning classifier are indicated at 770 and 780, respectively. In some instances, highlighted in cells outlined with dashed boxes, a gene set provided either a higher magnitude correlation or a higher importance than any individual feature upon which the gene set value was determined using ssGSEA, indicating the value of including gene sets as features. Usefulness of including ssGSEA is also shown in FIG. 9. FIG. 9 shows two GUI reports on a responsiveness prediction for the same subject using two different trained machine learning classifiers. The prediction on the left 910 was obtained by generating a prediction without using ssGSEA gene sets as features during training or prediction. The prediction on the right 920 was obtained by generating a prediction using ssGSEA gene sets as features during training and prediction. When ssGSEA-derived gene sets were included, fewer features exceeded the minimum threshold boundary (11 versus 15), including some gene sets (which by definition were not included in the prediction obtained without gene sets 910), without sacrificing overall prediction (e.g., in both cases the prediction exceeded the 5.0 score set as a minimum response prediction classification score triggering classification of a subject as a responder).

Figure 8:
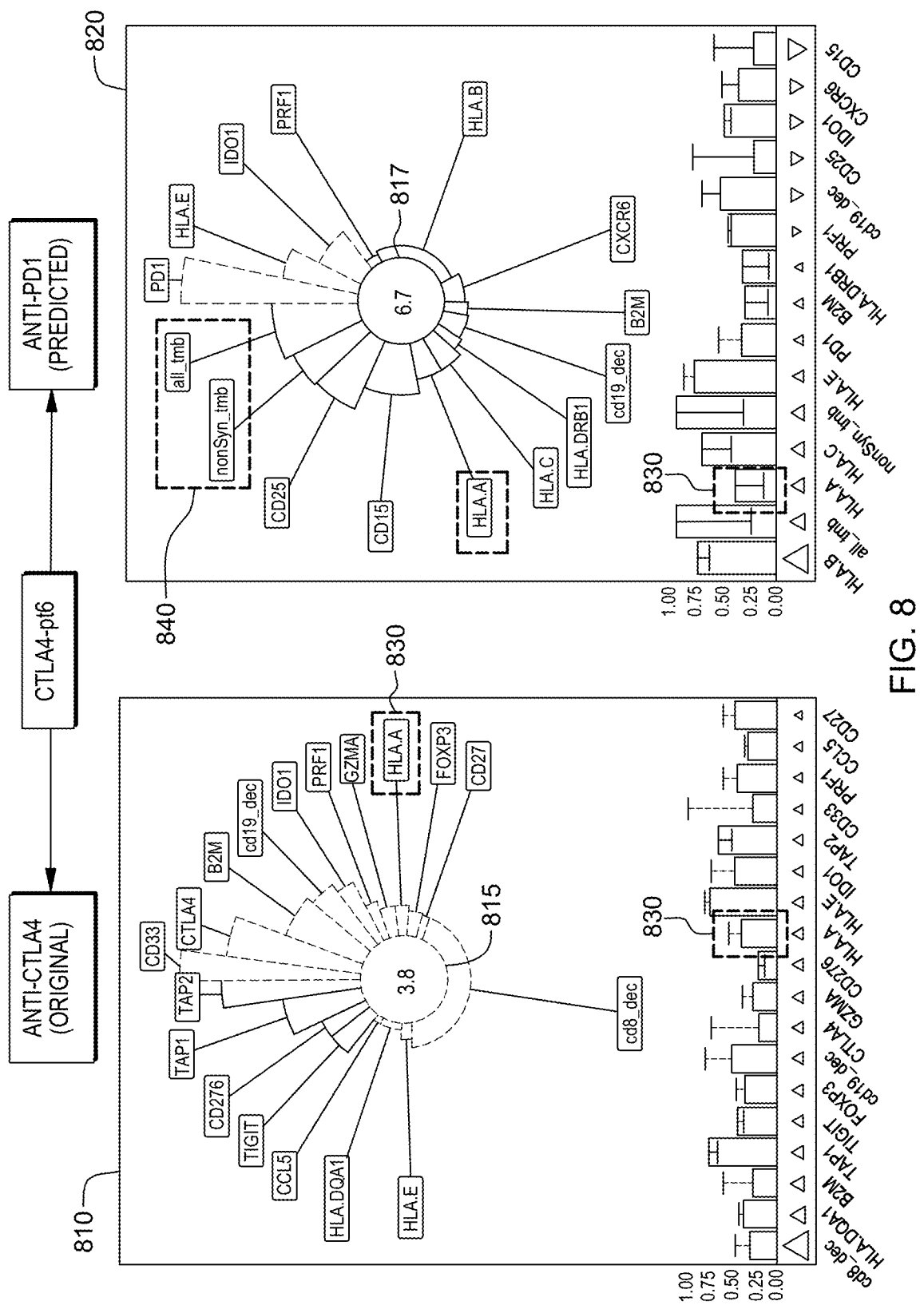
FIG. 8 is an example of a method of reporting and comparing a subject's responsiveness to different treatments as predicted by a trained machine learning-based classifier in accordance with aspects of the present disclosure.

FIG. 8 shows two GUI reports obtained from the same patient for whom a prediction was generated using two different machine learning classifiers, one trained to predict responsiveness to anti-CTLA4 treatment 810 and the other trained to predict responsiveness to anti-PD1 820, both using the features depicted in FIG. 2. The anti-CTLA4 machine learning classifier 810 produced a response prediction classification score of 3.8 predicting that the subject would not respond to anti-CTLA4 treatment (using a response prediction classification score threshold of 5.0). In this case 810, the valence of the responsiveness prediction classification score (non-responsiveness) is indicated with dotted lines around an inner circle in which the response prediction classification score is depicted 815. Accuracy of such prediction is corroborated by the response classification of this patient from the source clinical study (Van Allen et al.) as "disease progression," indicating that the subject was non-responsive to anti-CTLA4 treatment. However, the anti-PD1 machine learning classifier 820 generated a response prediction classification score of 6.7 predicting that the subject would respond to anti-PD1 (e.g., anti-PD1 or anti-PD-L1 antibody) treatment (again using a response prediction classification score threshold of 5.0). In this case 820, the response prediction classification score (responsiveness) is indicated with a solid line around an inner circle in which the response prediction classification score is depicted 817.

Different response prediction classification scores (and corresponding differences in valence, weight, and importance of various features) depending on which machine learning classifier is used reflects the power of methods as disclosed herein. For example, indicators reported for HLA.A 830 indicate that it has a negative valence for predicting responsiveness of this patient to anti-CTLA4 treatment but a positive valence for predicting this subject's responsiveness to anti-PD1 treatment. Furthermore, values of features for nonsynonymous tumor mutation burden and all tumor mutational burden did not surpass the minimum importance threshold in the anti-CTLA4 machine learning classifier but did for the anti-PD1 machine learning classifier 840.

As with the example depicted in FIG. 5, the exemplary GUI reports depicted in FIGS. 6, 8, 9, and 10 could include user interactivity. Thus, for some examples, a user could have the option of accessing drop down menus from different aspects of the GUI such as by touching a portion of a touchscreen display corresponding to a portion of the GUI report or moving a graphical element such as a cursor with a device such as a mouse over a feature (e.g., annulus sector or column in a histogram or other indicators) to access additional information or select from additional analysis that could be run via different programming instructions on the one or more microprocessors stored on the one or more memory stores.

Figure 11A:
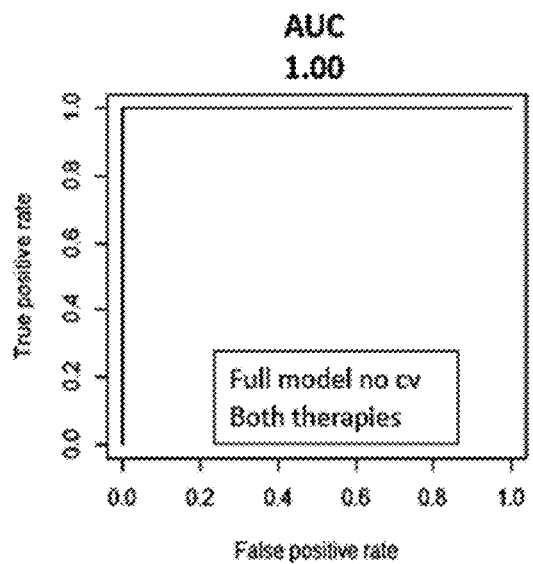
FIGS. 11A-11D are comparative graphs and figures demonstrating that using 38 features generates a superior classifier performance compared to using single factors.
Figure 11B:
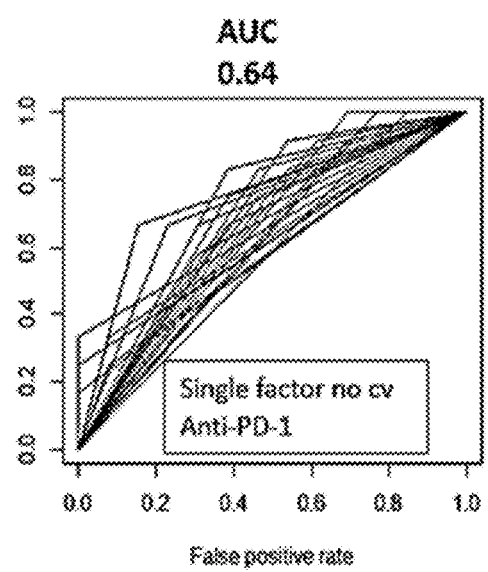
Figure 11C:
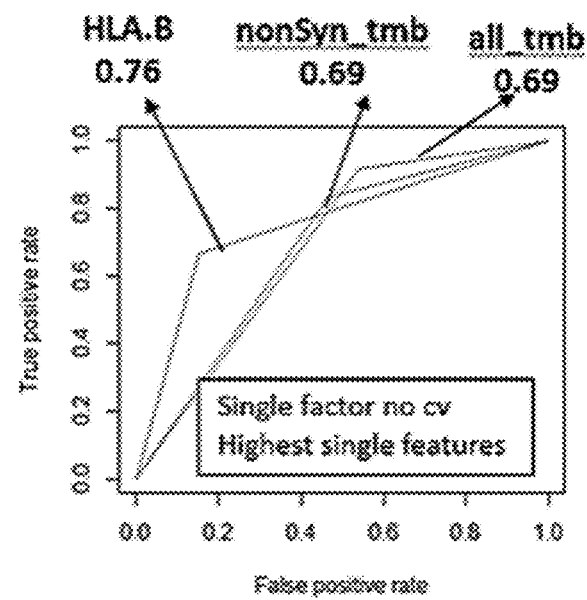
Figure 11D:
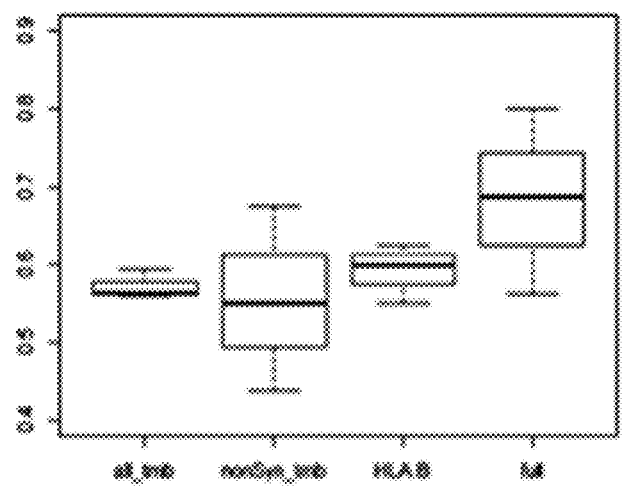

FIGS. 11A-11D demonstrate that using all of the 38 features depicted in FIG. 2 generates a classifier performance than using single factors. This was true for machine learning classifiers whether trained to predict responsiveness to anti-PD1 or anti-CTLA4 treatment. FIG. 11A shows that using all 38 features for training and testing a machine learning classifier to predict responsiveness to, for example, anti-PD1 treatment, yielded an AUC of the Receiver Operator Characteristic (auROC) of false- vs true-positives of 1.00 when the machine learning classifier is over-trained without cross-validation (CV), reaching 1.00 auROC, vs. 0.64 auROC for averaged single factors as shown in FIG. 11B. FIGS. 11C and 11D further show that using the 38 features depicted in FIG. 2 is more accurate than all three of the top single factor features, HLA-B, nonSyn_tmb and all_tmb.

Figure 12A:
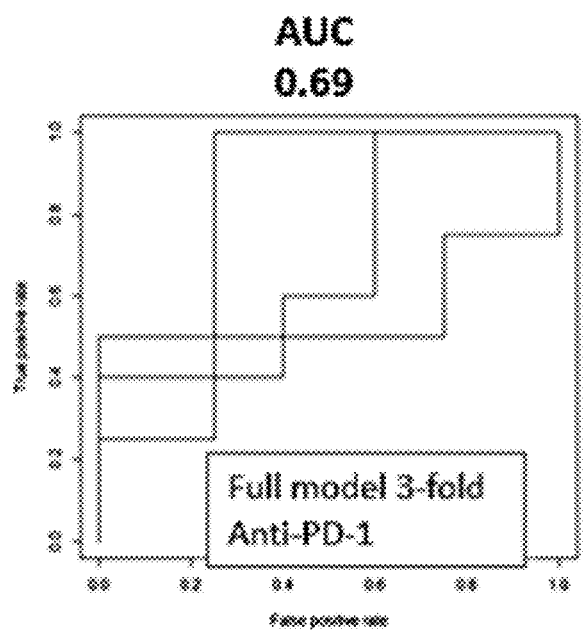
FIGS. 12A-12D are graphs and figures comparing performance of machine learning classifiers using 38 features without gene sets or 44 features with gene sets.
Figure 12B:
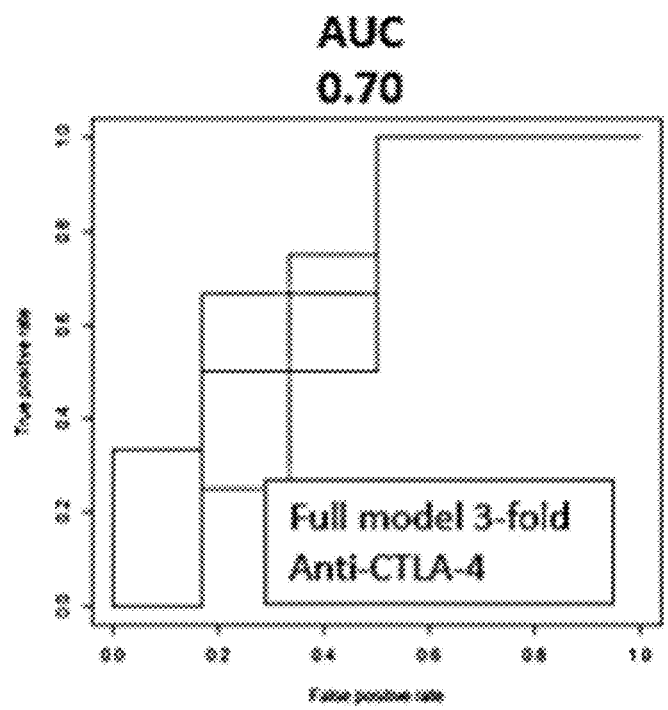
Figure 12C:
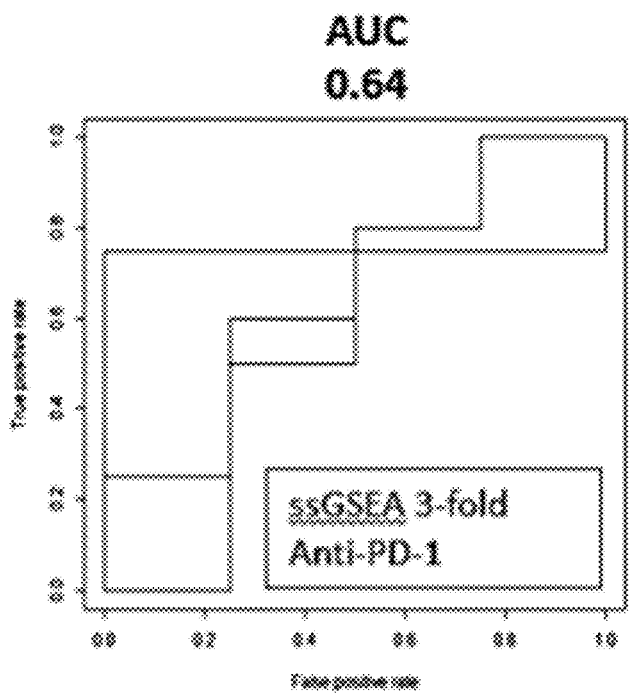
Figure 12D:
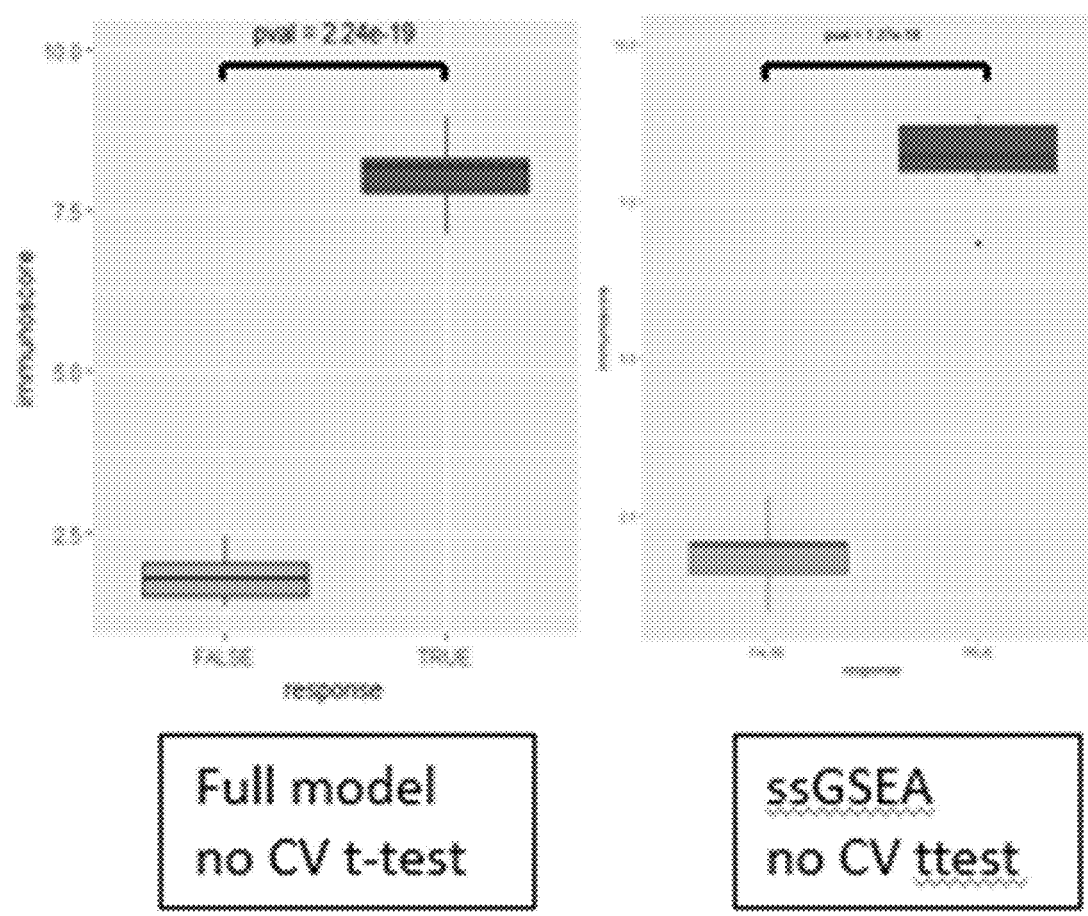

FIGS. 12A-12D are graphs showing the effects using gene sets obtained via ssGSEA had on classifier performance. Performance of ssGSEA is comparable to using the 38 features depicted in FIG. 2. FIGS. 12A, 12B, and 12C report 3-fold cross validation auROC for using the 38 features depicted in FIG. 2 for predicting responsiveness to anti-PD1 (FIG. 12A) or anti-CTLA4 (FIG. 12B) treatment, or using the 38 features plus the 6 gene sets depicted in FIG. 7 for predicting responsiveness to anti-PD1 treatment (FIG. 12C). Although performance was reduced from 0.69 to 0.64 for anti-PD1 treatment prediction when the 6 gene sets attained via ssGSEA were included (comparing FIG. 12A to FIG. 12C), the number of features with importance that exceeded the minimum importance threshold was reduced from 15 to 11 (as discussed above; see e.g. FIG. 8). FIG. 12D shows comparable t-test results for false and true positive results by response prediction classification score for machine learning classifiers (without cross-validation). In some examples, including gene sets as features therefore may improve overall robustness of a classifier, help avoid over-training, and enables a cleaner interpretation of important features and indicators therefor.

The data used in these examples were from subjects enrolled in a study to test effectiveness of checkpoint inhibitors anti-CTLA4 antibody, anti-PD1 antibody, and anti-PD1-L1 antibodies in patients with melanoma. However, as would be understood by skilled persons based on the role checkpoint inhibits are known to play in blunting effectiveness of immuno-oncology treatment of other cancers, and the role of features such as those included here in checkpoint pathway function, methods, systems, and classifiers as disclosed herein would be equally useful and effective in generating predictions of subject responsiveness to these checkpoint inhibitors in other cancers as well, including breast cancer, cancers of the digestive system, liver cancer, bladder cancer, lymphoma, leukemia, cancers of bone tissue, cancers of the nervous system, lung cancers, pancreatic cancers, or others. Furthermore, as would also be understood by skilled persons, responsiveness to checkpoint inhibitors in addition to those specifically used in the foregoing examples disclosed here may also be predicted using methods, systems, and classifiers as disclosed herein, which serve merely as non-limiting examples of the applicability thereof.

The pitfall of this performance analysis is the low sample size. Even with dozens of features, over-training is unavoidable. Meanwhile, fold cross-validation results are highly unstable, showing discretized auROC points, instead of a continuous curve. However, within the limitation we have, full model clearly out-performs single factors.

Although preferred embodiments have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. A method for administering a cancer treatment, comprising:
   a) obtaining a responsiveness score for a non-training subject having cancer, said obtaining comprising:
      i) inputting total mutational burden, tumor infiltration, and factor expression of the non-training subject to a machine learning classifier;
      wherein total mutational burden comprises one or both of all mutations and nonsynonymous mutations, tumor infiltration comprises any one or more of tumor infiltration by cells expressing cluster of differentiation 8 (CD8), tumor infiltration by cells expressing cluster of differentiation 4 (CD4), and tumor infiltration by cells expressing cluster of differentiation 19 (CD19), and factor expression comprises any one or more of beta 2 microglobulin (B2M) expression, proteasome subunit beta 10 (PSMB10) expression, antigen peptide transmitter 1 (TAP1) expression, antigen peptide transporter 2 (TAP2) expression, human leukocyte antigen A (HLA-A) expression, major histocompatibility complex class I B (HLA-B) expression, major histocompatibility complex class I C (HLA-C) expression, major histocompatibility complex class II DQ alpha 1 (HLA-DQA1) expression, HLA class II histocompatibility antigen DRB1 beta chain (HLA-DRB1) expression, HLA class I histocompatibility antigen alpha chain E (HLA-E) expression, natural killer cell granule protein 7 (NKG7) expression, chemokine like receptor 1 (CMKLR1) expression, granzyme A (GZMA) expression, perforin-1 (PRF1) expression, cytotoxic T-lymphocyte-associated protein 4 (CTLA4) expression, programmed cell death protein 1 (PD1) expression, programmed death-ligand 1 (PDL1) expression, programmed cell death 1 ligand 2 (PDL2) expression, lymphocyte-activation gene 3 (LAG3) expression, T cell immunoreceptor with Ig and ITIM domains (TIGIT) expression, cluster of differentiation 276 (CD276) expression, chemokine (C-C motif) ligand 5 (CCL5) expression, cluster of differentiation 27 (CD27) expression, chemokine (C-X-C motif) ligand 9 (CXCL9) expression, C-X-C motif chemokine receptor 6 (CXCR6) expression, indoleamine 2,3-dioxygenase (IDO) expression, signal transducer and activator of transcription 1 (STAT1) expression, 3-fucosyl-N-acetyl-lactosamine (CD15) expression, interleukin-2 receptor alpha chain (CD25) expression, siglec-3 (CD33) expression, cluster of differentiation 39 (CD39) expression, cluster of differentiation (CD118) expression, and forkhead box P3 (FOXP3) expression;
      wherein the machine learning classifier is selected from the group consisting of a neural network classifier, a support vector machine, a max entropy classifier, an extreme gradient boosting classifier, a random fern classifier, and a random forest classifier,
      and wherein the machine learning classifier was trained on said total mutational burden, tumor infiltration, and factor expression of a plurality of training subjects having cancer and a responsiveness of each of said plurality of training subjects to cancer treatment to predict responsiveness of said non-training subject to said cancer treatment; and
      ii) generating, using the machine-learning classifier, a responsiveness score for the non-training subject; and
   b) administering, based on said obtaining, the cancer treatment to the non-training subject for responsiveness scores that equal or exceed a predetermined threshold of 5;
   wherein the cancer treatment is a checkpoint inhibitor selected from an anti-CTLA4 drug, an anti-PD1 drug, an anti-PDL1 drug, and any combination of two or more of said drugs.

2. The method of claim 1, wherein, for the non-training subject, for one or more of the plurality of training subjects, or for the non-training subject and one or more of the plurality of training subjects, at least some of the total mutational burden, at least some of the tumor infiltration, at least some of the factor expression, or any combination of two or more of the foregoing, comprise gene sets.

3. The method of claim 2 wherein the gene sets were selected using single sample gene set enrichment analysis.

4. The method of claim 1, wherein at least one total mutational burden, at least one tumor infiltration, or at least one factor expression, comprises an identifier selected from a valence, an importance, and a weight, and further comprising visually reporting the identifier by displaying a graphical user interface on a display connected to a computer or computer system comprising one or more microprocessor and one or more memory wherein the identifier of the non-training subject is stored, wherein the graphical user interface reports identifiers as aspects of an annulus sector, wherein an angle of the annulus sector reports the importance, an outer radius of the annulus sector reports the weight, and a color of the annulus sector reports the valence.

5. The method of claim 4 wherein the identifier comprises an importance and the importance comprises a Gini index decrease.

6. The method of claim 5 wherein the graphical user interface reports the identifier if and only if the importance is above a threshold.

7. The method of claim 6 wherein the importance is not above the threshold if the square of the importance is not above 0.1.

8. The method of claim 6, wherein each of the annulus sectors comprises an inner arc and the inner arcs of the annulus sectors are arranged to form a circle.

9. The method of claim 1, further comprising inputting, or having input, to the trained machine learning classifier a responsiveness of the non-training subject to the cancer treatment and further training the machine learning classifier, wherein further training comprises training, or having trained, the trained machine learning classifier on one or more of total mutational burden, tumor infiltration, and factor expression of a tumor sample obtained from the non-training subject and a responsiveness of the non-training subject to the cancer treatment.

10. The method of claim 1, wherein the cancer treatment is selected from an anti-CTLA4 antibody, an anti-PD1 antibody, an anti-PDL1 antibody, and any combination of two or more of the foregoing.

11. The method of claim 1, wherein
total mutational burden comprises all mutations and non-synonymous mutations.

12. The method of claim 11, wherein the cancer treatment is selected from an anti-CTLA4 antibody, an anti-PD1 antibody, an anti-PDL1 antibody, and any combination of two or more of the foregoing.

13. The method of claim 1, wherein
tumor infiltration comprises tumor infiltration by cells expressing cluster of different 8 (CD8), tumor infiltration by cells expressing cluster of differentiation 4 (CD4), and tumor infiltration by cells expressing cluster of differentiation 19 (CD19).

14. The method of claim 13, wherein the cancer treatment is selected from an anti-CTLA4 antibody, an anti-PD1 antibody, an anti-PDL1 antibody, and any combination of two or more of the foregoing.

15. The method of claim 1, wherein the machine learning classifier is a random forest classifier.

16. The method of claim 15, wherein 50,000 trees are used in training the random forest classifier.

* * * * *

UNITED STATES PATENT AND TRADEMARK OFFICE
CERTIFICATE OF CORRECTION

PATENT NO. : 12,266,426 B2
APPLICATION NO. : 16/208149
DATED : April 1, 2025
INVENTOR(S) : Zhang et al.

It is certified that error appears in the above-identified patent and that said Letters Patent is hereby corrected as shown below:

In the Specification

Column 2, Line 48: Delete "beta 2 microglobulin (B2M)," and insert -- beta-2 microglobulin (B2M), --

Column 4, Line 17: Delete "beta 2 microglobulin (B2M)," and insert -- beta-2 microglobulin (B2M), --

Column 5, Line 31: Delete "machine-learning" and insert -- machine learning --

Column 11, Line 41-42: Delete "beta 2 microglobulin (B2M)," and insert -- beta-2 microglobulin (B2M), --

Column 14, Line 6-7: Delete "beta 2 microglobulin (B2M)," and insert -- beta-2 microglobulin (B2M), --

Column 25, Line 44: Delete "machine learning" and insert -- machine-learning --

In the Claims

Column 34, Line 3: Claim 1, Delete "beta 2 microglobulin (B2M)," and insert -- beta-2 microglobulin (B2M), --

Column 34, Line 49: Claim 1, Delete "to cancer" and insert -- to said cancer --

Column 35, Line 3: Claim 3, Delete "claim 2" and insert -- claim 2, --

Column 35, Line 18: Claim 5, Delete "claim 4" and insert -- claim 4, --

Signed and Sealed this
Twenty-second Day of July, 2025

Coke Morgan Stewart
*Acting Director of the United States Patent and Trademark Office*

CERTIFICATE OF CORRECTION (continued)
U.S. Pat. No. 12,266,426 B2

Column 35, Line 21: Claim 6, Delete "claim 5" and insert -- claim 5, --

Column 35, Line 24: Claim 7, Delete "claim 6" and insert -- claim 6, --

Column 36, Line 21: Claim 13, Delete "different" and insert -- differentiation --